(12) United States Patent
Peyman

(10) Patent No.: US 10,606,066 B2
(45) Date of Patent: Mar. 31, 2020

(54) FLUIDIC LIGHT FIELD CAMERA

(71) Applicant: Gholam A. Peyman, Sun City, AZ (US)

(72) Inventor: Gholam A. Peyman, Sun City, AZ (US)

(*) Notice: Subject to any disclaimer, the term of this patent is extended or adjusted under 35 U.S.C. 154(b) by 0 days.

(21) Appl. No.: 16/112,595

(22) Filed: Aug. 24, 2018

(65) Prior Publication Data
US 2019/0011691 A1 Jan. 10, 2019

Related U.S. Application Data

(60) Continuation-in-part of application No. 15/608,745, filed on May 30, 2017, now Pat. No. 10,133,056,
(Continued)

(51) Int. Cl.
*A61B 3/10* (2006.01)
*G02C 5/00* (2006.01)
(Continued)

(52) U.S. Cl.
CPC .......... *G02B 26/004* (2013.01); *A61B 1/0019* (2013.01); *A61B 3/12* (2013.01); *A61B 3/1225* (2013.01); *A61B 3/14* (2013.01); *A61F 2/1635* (2013.01); *A61F 2/1648* (2013.01); *A61F 2/1651* (2015.04); *G02B 3/14* (2013.01); *G02B 7/28* (2013.01); *G02B 26/0825* (2013.01);
(Continued)

(58) Field of Classification Search
CPC ........... A61B 3/103; A61B 3/14; A61B 3/113; A61B 3/125; A61B 3/024; A61B 3/1015; G02C 5/00; G02C 7/02

USPC ....... 351/200, 205–206, 210, 219, 222, 246, 351/41, 159, 160 R, 161, 176
See application file for complete search history.

(56) References Cited

U.S. PATENT DOCUMENTS

| 4,373,218 A | 2/1983 | Schachar |
| 4,573,998 A | 3/1986 | Mazzocco |

(Continued)

OTHER PUBLICATIONS

De-Ying Zhang, Nicole Justis, Yu-Hwa Lo, "Integrated Fluidic Adaptive Zoom Lens", Optics Letters, vol. 29, Issue No. 24, pp. 2855-2857, dated Dec. 15, 2004.
(Continued)

*Primary Examiner* — Dawayne Pinkney
(74) *Attorney, Agent, or Firm* — The Law Office of Patrick F. O'Reilly III, LLC

(57) ABSTRACT

A fluidic light field camera is disclosed herein. The fluidic light field camera includes a fluidic objective lens; a fluid control system operatively coupled to the fluidic objective lens, the fluid control system to change the shape of the fluidic objective lens in accordance with the amount of fluid therein; a microlens array disposed behind the fluidic objective lens; a sensor array disposed behind the microlens array; and a data processing device operatively coupled to the fluid control system and the sensor array, the data processing device configured to vary the focal point of the fluidic light field camera by using the fluid control system to control the shape of the fluidic objective lens, thereby enabling all portions of an image being captured by the fluidic light field camera to be in focus during a single recording cycle of the fluidic light field camera.

13 Claims, 14 Drawing Sheets

Related U.S. Application Data which is a division of application No. 14/942,256, filed on Nov. 16, 2015, now Pat. No. 9,671,607, and a continuation-in-part of application No. 14/461,263, filed on Aug. 15, 2014, now Pat. No. 9,191,568, which is a continuation-in-part of application No. 13/793,199, filed on Mar. 11, 2013, now Pat. No. 9,016,860, which is a continuation-in-part of application No. 13/165,231, filed on Jun. 21, 2011, now Pat. No. 8,409,278.

(60) Provisional application No. 62/549,941, filed on Aug. 24, 2017, provisional application No. 62/563,582, filed on Sep. 26, 2017, provisional application No. 62/671,525, filed on May 15, 2018, provisional application No. 62/180,668, filed on Jun. 17, 2015.

(51) Int. Cl.

| | | |
|---|---|---|
| A61B 3/14 | (2006.01) | |
| A61B 3/00 | (2006.01) | |
| G02B 1/06 | (2006.01) | |
| G02B 26/00 | (2006.01) | |
| G02B 3/14 | (2006.01) | |
| H04N 5/232 | (2006.01) | |
| G03B 13/32 | (2006.01) | |
| G02C 7/04 | (2006.01) | |
| G02B 26/08 | (2006.01) | |
| G02B 7/28 | (2006.01) | |
| A61F 2/16 | (2006.01) | |
| A61B 3/12 | (2006.01) | |
| A61B 1/00 | (2006.01) | |
| G03B 17/17 | (2006.01) | |
| G03B 13/34 | (2006.01) | |
| H04N 5/225 | (2006.01) | |
| H04N 5/369 | (2011.01) | |
| G02C 7/08 | (2006.01) | |

(52) U.S. Cl.
CPC .............. *G02C 7/04* (2013.01); *G03B 13/32* (2013.01); *G03B 13/34* (2013.01); *G03B 17/17* (2013.01); *H04N 5/22541* (2018.08); *H04N 5/23212* (2013.01); *H04N 5/3696* (2013.01); *A61B 3/102* (2013.01); *G02C 7/085* (2013.01)

(56) References Cited

U.S. PATENT DOCUMENTS

| | | |
|---|---|---|
| 4,685,921 A | 8/1987 | Peyman |
| 4,731,078 A | 3/1988 | Stoy et al. |
| 4,816,031 A | 3/1989 | Pfoff |
| 5,182,585 A | 1/1993 | Stoner |
| 6,142,630 A | 11/2000 | Koester |
| 6,186,628 B1 | 2/2001 | Van de Velde |
| 6,595,642 B2 | 7/2003 | Wirth |
| 6,673,067 B1 | 1/2004 | Peyman |
| 6,806,988 B2 | 10/2004 | Onuki et al. |
| 6,947,782 B2 | 9/2005 | Schulman et al. |
| 7,182,780 B2 | 2/2007 | Terwee et al. |
| 7,413,306 B2 | 8/2008 | Campbell |
| 8,409,278 B2 | 4/2013 | Peyman et al. |
| 9,016,860 B2 | 4/2015 | Peyman |
| 9,191,568 B2 | 11/2015 | Peyman |
| 9,671,607 B2 | 6/2017 | Peyman |
| 10,133,056 B2 | 11/2018 | Peyman |
| 2002/0016629 A1 | 2/2002 | Sandstedt et al. |
| 2002/0118464 A1 | 8/2002 | Nishioka et al. |
| 2002/0149864 A1 | 10/2002 | Kaneko |
| 2003/0117719 A1 | 6/2003 | Wakai et al. |
| 2003/0147046 A1 | 8/2003 | Shadduck |
| 2005/0140922 A1 | 6/2005 | Bekerman et al. |
| 2006/0106426 A1 | 5/2006 | Campbell |
| 2007/0046948 A1 | 3/2007 | Odoleanu et al. |
| 2007/0139751 A1 | 6/2007 | Kuiper et al. |
| 2007/0156021 A1 | 7/2007 | Morse et al. |
| 2007/0188882 A1* | 8/2007 | Cernasov ............. G02B 3/0056 359/659 |
| 2007/0211207 A1 | 9/2007 | Lo et al. |
| 2008/0030682 A1 | 2/2008 | Teige et al. |
| 2008/0158508 A1 | 7/2008 | Kawashima et al. |
| 2010/0118414 A1 | 5/2010 | Bolis |
| 2010/0157438 A1 | 6/2010 | Griffith et al. |
| 2010/0265498 A1 | 10/2010 | Zhang |
| 2015/0049348 A1* | 2/2015 | Schmidt ................ G02B 21/14 356/630 |

OTHER PUBLICATIONS

First office action on the merits (Non-Final Rejection) in U.S. Appl. No. 13/793,199, dated Jan. 9, 2014.
Second office action on the merits (Final Rejection) in U.S. Appl. No. 13/793,199, dated Mar. 6, 2014.
Third office action on the merits (Non-Final Rejection) in Appl. No. 13/793,199, dated Jul. 18, 2014.
First office action on the merits (Non-Final Rejection) in U.S. Appl. No. 14/461,263, dated Dec. 24, 2014.
Second office action on the merits (Final Rejection) in U.S. Appl. No. 14/461,263, dated Jun. 11, 2015.
First office action on the merits (Non-Final Rejection) in U.S. Appl. No. 14/942,256, dated Apr. 19, 2016.
Second office action on the merits (Final Rejection) in U.S. Appl. No. 14/942,256, dated Oct. 3, 2016.
First office action on the merits (Non-Final Rejection) in U.S. Appl. No. 15/608,745, dated Jul. 26, 2017.
Second office action on the merits (Final Rejection) in U.S. Appl. No. 15/608,745, dated Dec. 27, 2017.
Third office action on the merits (Non-Final Rejection) in U.S. Appl. No. 15/608,745, dated May 2, 2018.
Rodriguez-Ramos et al., "The CAFADIS camera: a new tomographic wavefront sensor for Adaptive Optics"; dated Feb. 24, 2010; published by EDP Sciences; Abstract, pp. 1-2; and Article, pp. 1-6 (8 pages total).

* cited by examiner

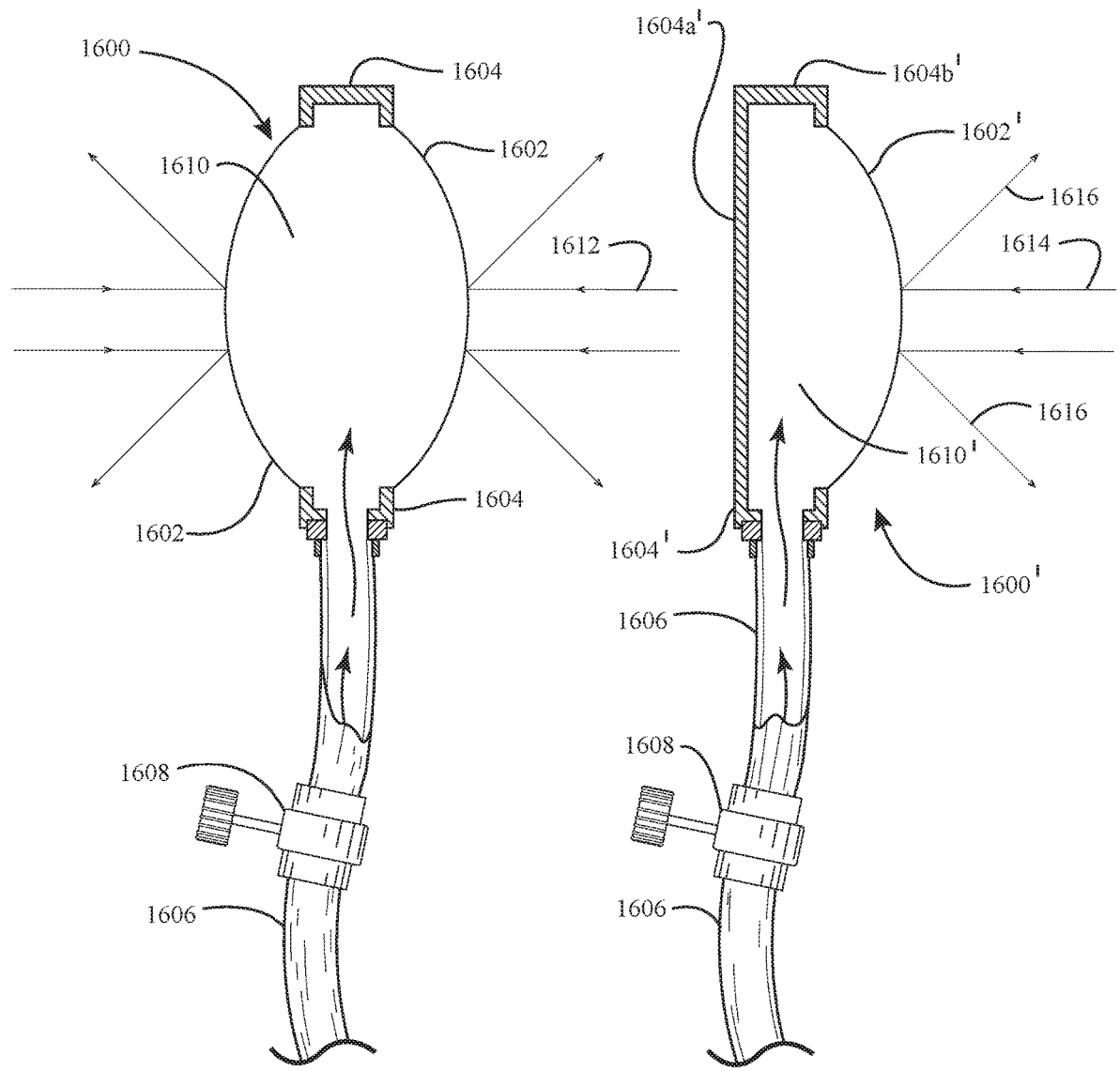

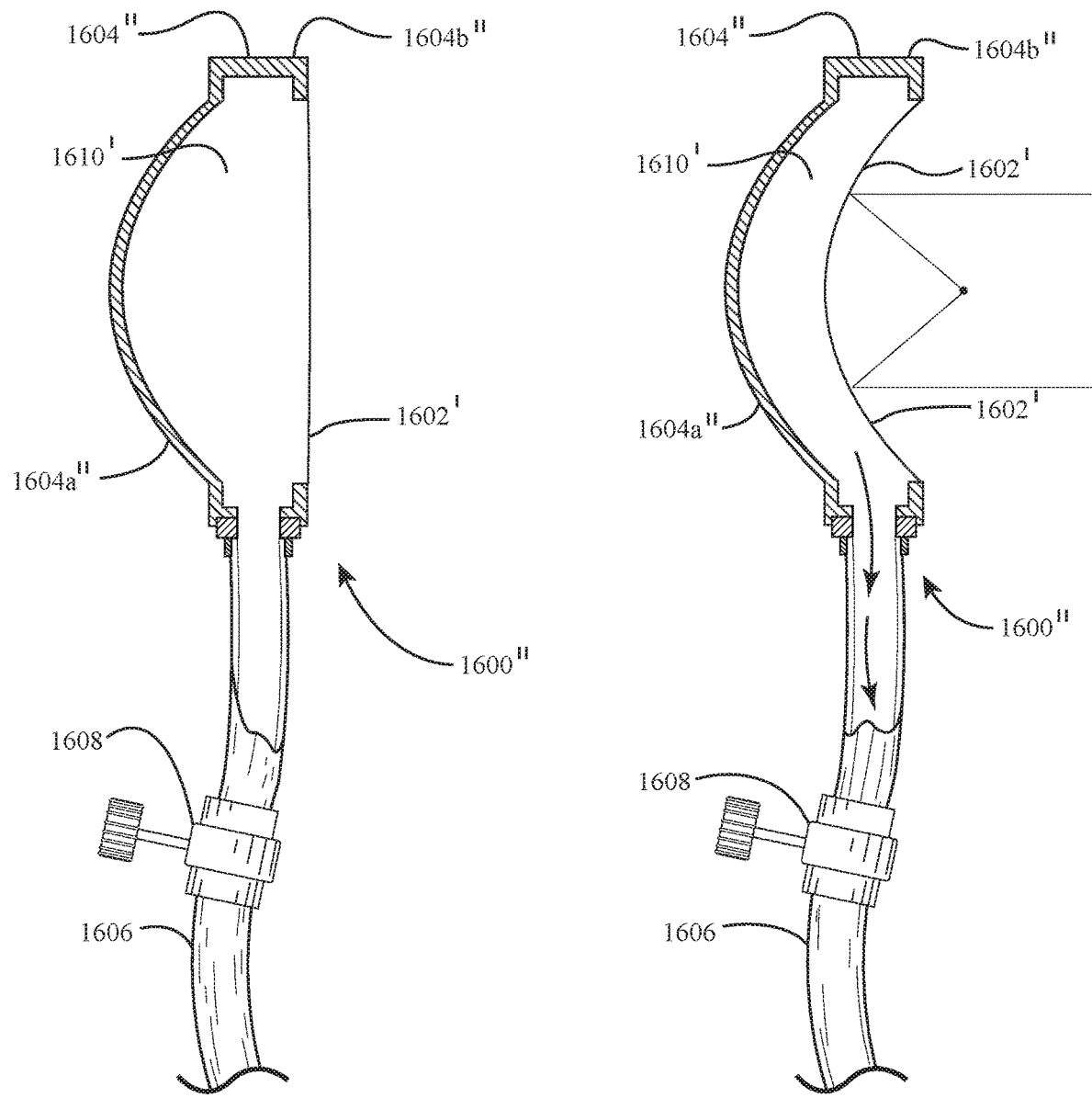

Section C-C

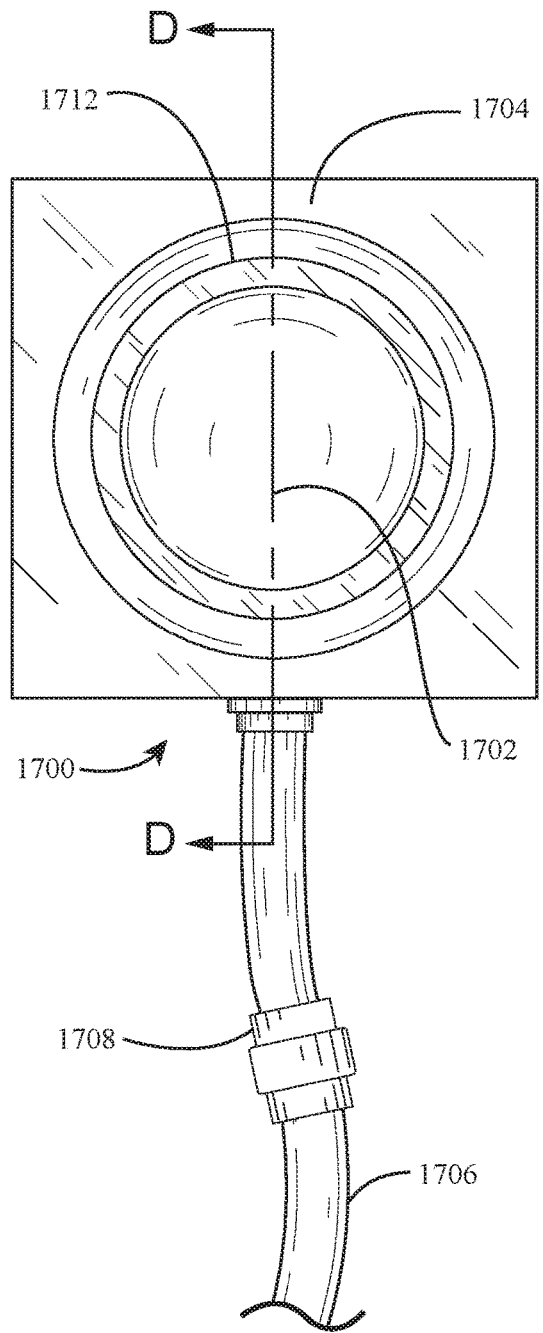
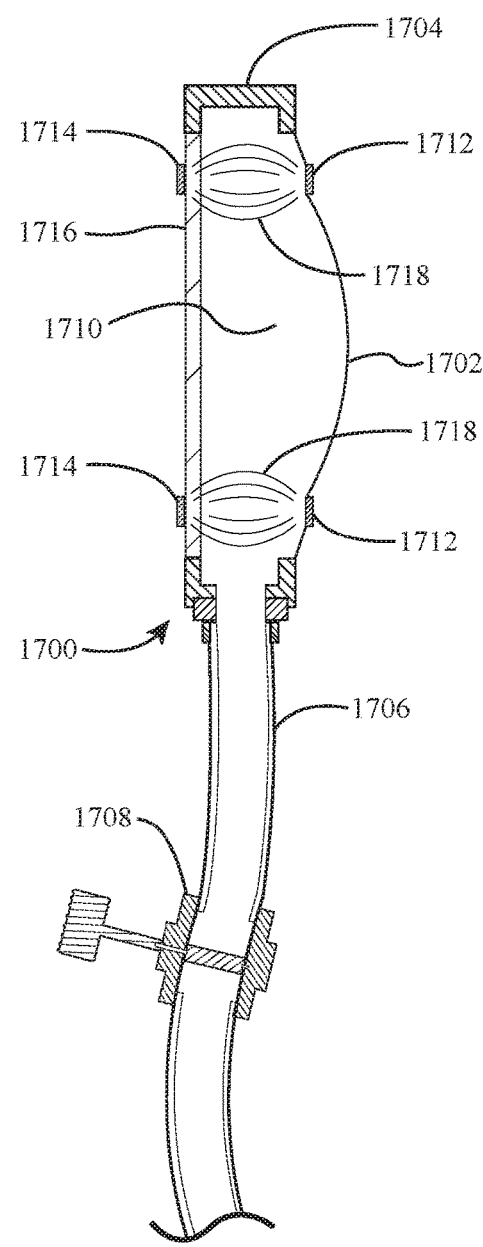
FIG. 14
Section D-D
FIG. 15

FLUIDIC LIGHT FIELD CAMERA

CROSS-REFERENCE TO RELATED APPLICATIONS

This patent application claims priority to U.S. Provisional Application No. 62/549,941, entitled "Dynamic Imaging System and a Remote Laser Treatment System Using the Same", filed on Aug. 24, 2017; U.S. Provisional Application No. 62/563,582, entitled "Dynamic Imaging System and a Remote Laser Treatment System Using the Same", filed on Sep. 26, 2017; and U.S. Provisional Patent Application No. 62/671,525, entitled "Dynamic Image Recognition System For Security And Telemedicine", filed on May 15, 2018; and this patent application is a continuation-in-part of application Ser. No. 15/608,745, entitled "Flexible Fluidic Mirror and Hybrid System", filed May 30, 2017; and Ser. No. 15/608,745 is a divisional application of U.S. patent application Ser. No. 14/942,256, entitled "Flexible Fluidic Mirror and Hybrid System", filed on Nov. 16, 2015, now U.S. Pat. No. 9,671,607, which claims priority to U.S. provisional application No. 62/180,668, entitled "Flexible Fluidic Mirror and Hybrid System", filed Jun. 17, 2015; and Ser. No. 14/942,256 is a continuation-in-part of application Ser. No. 14/461,263, entitled "Automated Camera System With One Or More Fluidic Lenses", filed Aug. 15, 2014, now U.S. Pat. No. 9,191,568; and Ser. No. 14/461,263 is a continuation-in-part of application Ser. No. 13/793,199 entitled "Fluidic Adaptive Optic Fundus Camera", filed Mar. 11, 2013, now U.S. Pat. No. 9,016,860; and Ser. No. 13/793,199 is a continuation-in-part of application Ser. No. 13/165,231 entitled "External Lens with Flexible Membranes for Automatic Correction of the Refractive Errors of a Person", filed Jun. 21, 2011, now U.S. Pat. No. 8,409,278; the entire contents of each of which are hereby incorporated by reference.

STATEMENT REGARDING FEDERALLY SPONSORED RESEARCH OR DEVELOPMENT

Not Applicable.

NAMES OF THE PARTIES TO A JOINT RESEARCH AGREEMENT

Not Applicable.

INCORPORATION BY REFERENCE OF MATERIAL SUBMITTED ON A COMPACT DISK

Not Applicable.

BACKGROUND OF THE INVENTION

1. Field of the Invention

The invention generally relates to a fluidic light field camera. More particularly, the invention relates to a fluidic light field camera wherein the focal point of the camera is able to be quickly and easily adjusted.

2. Background

Conventional cameras are known that require the users thereof to manually adjust the focus of a lens prior to taking a photograph so that the acquired image is in-focus. The manual adjustment of the camera lens is laborious and often inaccurate. Thus, what is needed is an automated camera system that comprises means for automatically focusing the camera without the necessity for manual adjustment by the user thereof, and without the need for moving parts on the camera itself. In particular, there is a need for a light field camera with automatic focal point adjustment.

BRIEF SUMMARY OF EMBODIMENTS OF THE INVENTION

Accordingly, the present invention is directed to a fluidic light field camera that substantially obviates one or more problems resulting from the limitations and deficiencies of the related art.

In accordance with one or more other embodiments of the present invention, a fluidic light field camera is provided. The fluidic light field camera includes a fluidic objective lens, the fluidic objective lens having an outer housing and a flexible membrane supported within outer housing, the flexible membrane at least partially defining a chamber that receives a fluid therein; a fluid control system operatively coupled to the fluidic objective lens, the fluid control system configured to insert an amount of the fluid into the chamber of the fluidic objective lens, or remove an amount of the fluid from the chamber of the fluidic objective lens, in order to change the shape of the fluidic objective lens in accordance with the amount of fluid therein; a microlens array disposed behind the fluidic objective lens, the microlens array including a plurality of microlenses, the plurality of microlenses configured to capture light rays entering the fluidic light field camera from varying distances away from the fluidic light field camera; a sensor array disposed behind the microlens array, the sensor array including a plurality of pixels, the plurality of microlenses configured to divert the light rays to different ones of the pixels of the sensor array so to provide directional information for the light rays entering the fluidic light field camera; and a data processing device operatively coupled to the fluid control system and the sensor array, the data processing device configured to vary the focal point of the fluidic light field camera by using the fluid control system to control the shape of the fluidic objective lens, thereby enabling all portions of an image being captured by the fluidic light field camera to be in focus during a single recording cycle of the fluidic light field camera.

In a further embodiment of the present invention, the fluid control system comprises a pump and one or more fluid distribution lines, at least one of the one or more fluid distribution lines fluidly coupling the pump to the fluidic objective lens so that the pump is capable of adjusting concavity and/or convexity of the fluidic objective lens.

In yet a further embodiment, the fluid control system comprises a servomotor or piezoelectric system for driving an actuator that is configured to adjust concavity and/or convexity of the fluidic objective lens.

In still a further embodiment, the fluidic objective lens further comprises a magnetically actuated subsystem configured to selectively deform the flexible membrane so as to increase or decrease the convexity of the flexible membrane of the fluidic objective lens.

In yet a further embodiment, the magnetically actuated subsystem of the fluidic light field camera comprises an annular or rectangular ring-shaped plate disposed on a front surface of the flexible membrane and a corresponding annular or rectangular ring-shaped electromagnet disposed on a rear surface of the outer housing or flexible membrane, the annular or rectangular ring-shaped electromagnet configured to selectively displace the annular or rectangular ring-shaped plate disposed on the front surface of the flexible membrane when an electrical current is selectively applied to the electromagnet, whereby the selective displacement of the annular or rectangular ring-shaped plate by the electromagnet increases or decreases the convexity of the flexible membrane.

In still a further embodiment, the microlens array and the sensor array are disposed in a concave configuration relative to the light rays entering the fluidic light field camera through the fluidic objective lens.

In yet a further embodiment, the data processing device is configured to vary the focal point of the fluidic light field camera in a time duration of less than one millisecond so that the fluidic light field camera is capable of creating a two-dimensional image, a three-dimensional image, and/or a video where all portions of the image or images being captured by the fluidic light field camera are in focus during the single recording cycle of the fluidic light field camera.

Additional features and advantages are described herein, and will be apparent from, the following Detailed Description and the figures.

It is to be understood that the foregoing general description and the following detailed description of the present invention are merely exemplary and explanatory in nature. As such, the foregoing general description and the following detailed description of the invention should not be construed to limit the scope of the appended claims in any sense.

BRIEF DESCRIPTION OF THE SEVERAL VIEWS OF THE DRAWINGS

The invention will now be described, by way of example, with reference to the accompanying drawings, in which:

FIG. 6 is a side sectional view of a biconvex, flexible fluidic mirror, according to an embodiment of the invention;

FIG. 7 is a side sectional view of a convex, flexible fluidic mirror, according to another embodiment of the invention, wherein the section is generally cut along the cutting-plane line A-A in FIG. 8;

FIG. 9 is a side sectional view of a flexible concave fluidic mirror, according to yet another embodiment of the invention, wherein the flexible membrane of the mirror is in its relaxed state;

FIG. 10 is another side sectional view of the flexible concave fluidic mirror of FIG. 9, wherein the flexible membrane of the mirror is in its deformed state, and wherein the section is generally cut along the cutting-plane line B-B in FIG. 11;

FIG. 14 is a front/top view of a hybrid flexible fluidic mirror, according to yet another embodiment of the invention, wherein the mirror has a circular shape and a convex configuration;

FIG. 15 is a side sectional view of the hybrid flexible fluidic mirror of FIG. 14, wherein the section is generally cut along the cutting-plane line D-D in FIG. 14;

Throughout the figures, the same parts are always denoted using the same reference characters so that, as a general rule, they will only be described once.

DETAILED DESCRIPTION OF EMBODIMENTS OF THE INVENTION

Figure 1:
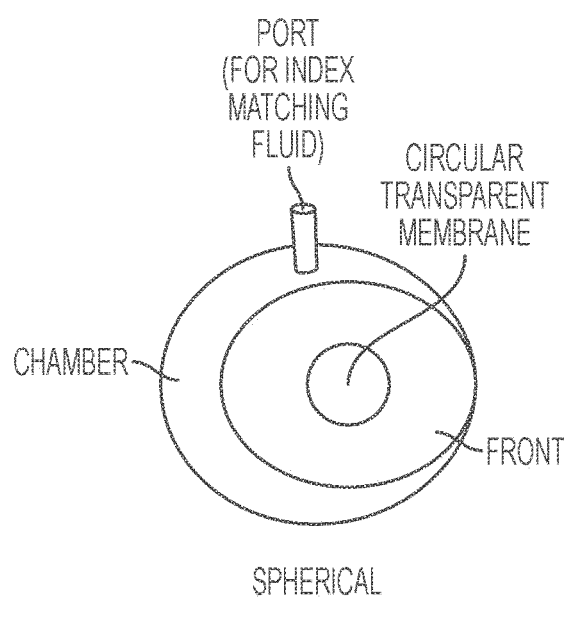
FIG. 1 illustrates a fluidic spherical lens in accordance with one embodiment of the present invention.
Figure 2:
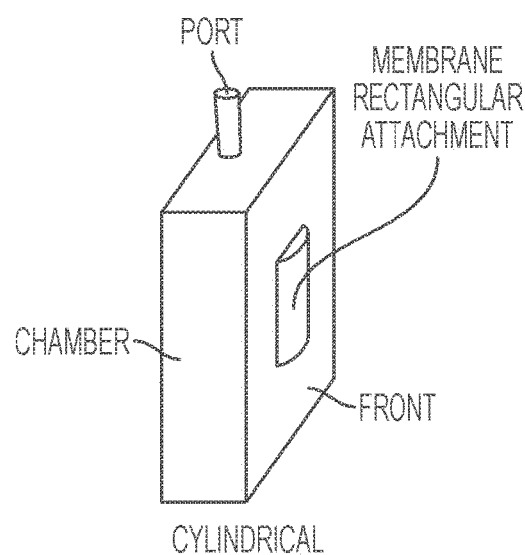
FIG. 2 illustrates a fluidic cylindrical lens in accordance with one embodiment of the present invention.
Figure 3:
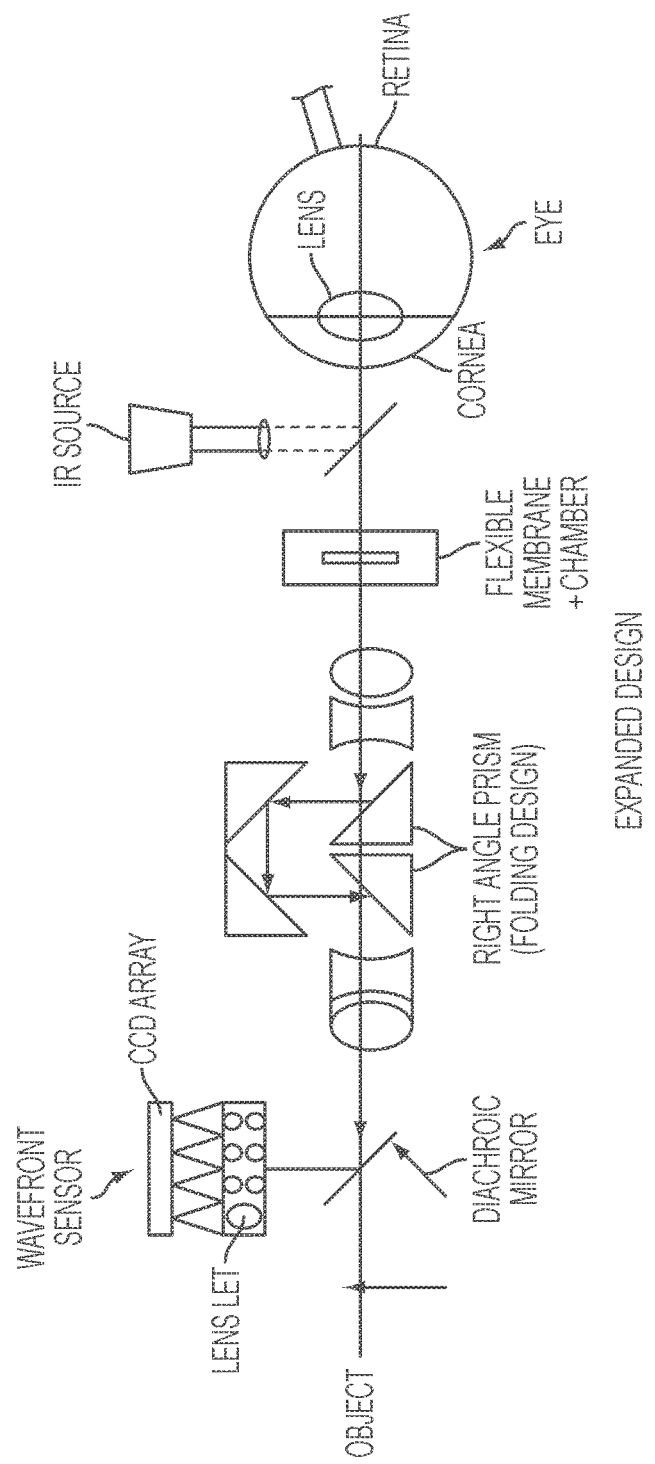
FIG. 3 illustrates another embodiment of the present invention in which a device is shown that is capable of automatically correcting all refractive errors of an eye.

Referring initially to FIGS. 1-3, one embodiment of the automated system of the present invention comprises a flexible membrane attached to a solid chamber where the membrane's surface can be made to act as a positive or negative surface by altering the fluid pressure inside the chamber.

The membrane can be constructed from any transparent elastomeric material. Depending on the membrane's peripheral attachment (e.g. circular) the membrane acts as a spherical (plus or minus 35.00 D) lens or (plus or minus 8.00 D) cylindrical lens when its attachment is rectangular (FIGS. 1 and 2).

By combining one spherical and two cylindrical lens-membranes, positioned 45 degrees to one another, one can correct all low order aberration of the refractive errors.

Using a non-uniform thickness membrane or an additional lens module one can also correct the higher order aberrations of refractive errors and creation of an achromatic lens. The flexible membrane lens is adjusted to null the wavefront error of the eye.

When this system is combined with a relay telescope, the image of the eye pupil can be projected onto a wavefront sensor via a diachroic mirror to analyze the shape of the wavefront (FIG. 3) while the person sees a near or distant object. The present system eliminates deformable mirrors and scanning parts; therefore it is a compact and stable unit.

The sensor in return corrects automatically all refractive errors of an eye by adding or subtracting fluid from the chamber holding the flexible membrane, thereby adjusting the curvature of the flexible membranes.

The final information is equal to the eye's refractive power of an eye for any given distance. Because of its simple design and light weight of the system both eyes of a person can be corrected simultaneously.

Additional application of this concept besides vision correction and photography includes microscope lenses, operating microscope, a lensometer capable of measuring accurately various focal points (power) of a multifocal lens or a multifocal diffractive lens, liquid crystal lenses etc. known in the art. A combination of the plus and minus flexible membrane lenses can also provide a lightweight telescope. Others include hybrid combination of this technology with diffractive, refractive and liquid crystal lenses.

Figure 4:
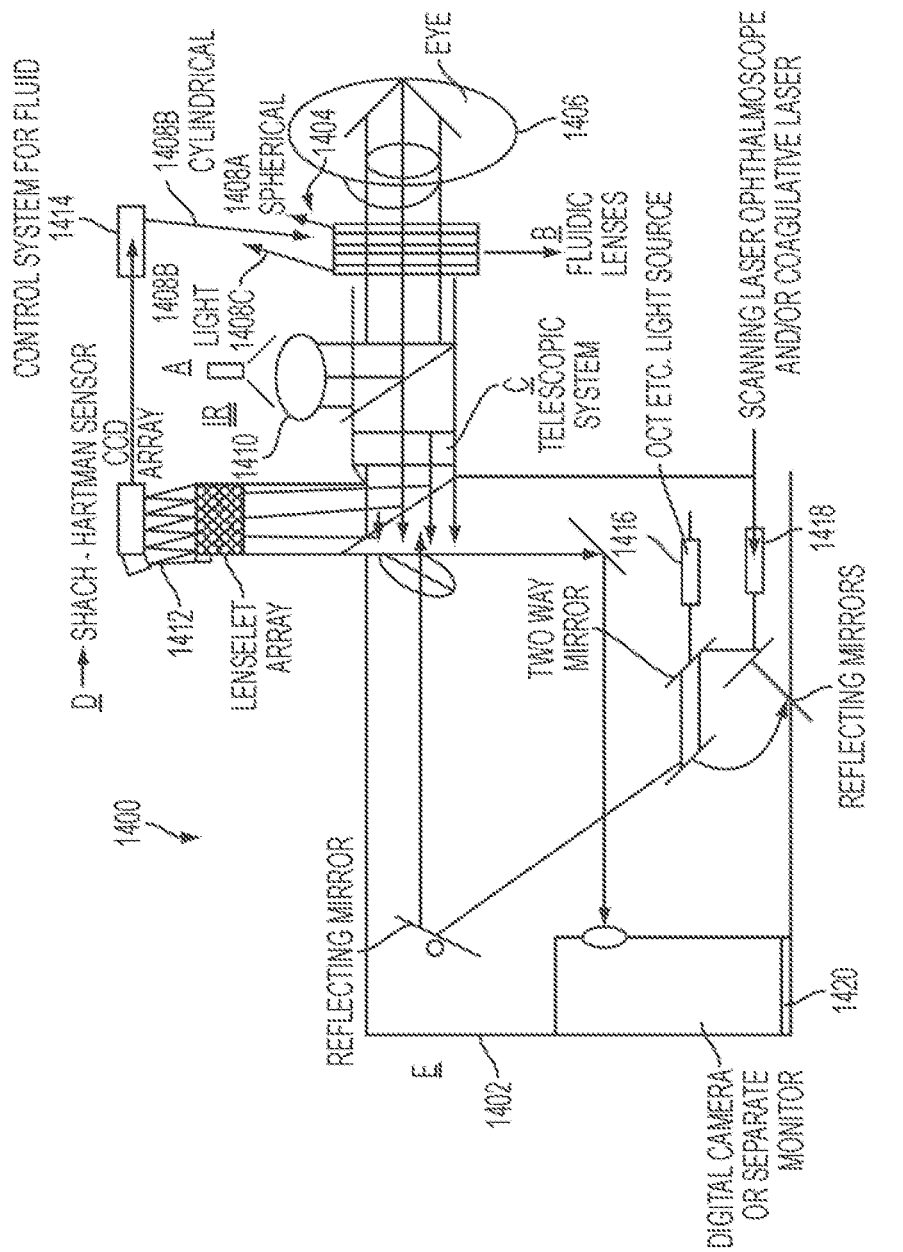
FIG. 4 illustrates another embodiment of the present invention in which a fluidic adaptive optic fundus camera is shown.

FIG. 4 illustrates another embodiment of the present invention. In particular, FIG. 4 illustrates a system 1400 in which a fundus camera 1402 uses a fluidic adaptive optic lens 1404. Adjacent the patient's eye 1406, are the three fluidic lenses 1408A-C. Preferably, one of the fluidic lenses is a spherical lens 1408A, and two of the lenses are cylindrical lenses 1408B and 1408C. However, the system can include any number of suitable lenses. In an exemplary embodiment, the spherical lens 1408A is disposed in a first plane, the first cylindrical lens 1408B is disposed in a second plane, and the second cylindrical lens 1408C is disposed in a third plane. Each of the first, second, and third planes are oriented parallel or generally parallel to one another. Also, the first cylindrical lens 1408B has a first axis and the second cylindrical lens 1408C has a second axis. The first axis of the first cylindrical lens 1408B is disposed at an angle of approximately 45 degrees relative to the second axis of the second cylindrical lens 1408C. In addition, in an exemplary embodiment, the first plane of the spherical lens 1408A is disposed closer to the eye 1406 than the second plane of the first cylindrical lens 1408B and the third plane of the second cylindrical lens 1408C. As such, in this exemplary embodiment, the cylindrical lenses 1408B, 1408C are positioned at 45 degrees or about 45 degrees relative to each other, and are disposed in front of the spherical lens 1408A (i.e., farther from the eye 1406).

The three lens system forms a telescopic system that transmits the light from IR light 1410 reflected from the eye and through the three lenses to a Shack-Hartmann sensor 1412. The Shack-Hartmann sensor is connected to control system 1414 through a charge-coupled device (CCD) array. The Shack-Hartmann sensor and the control system controls the amount of fluid injected and/or removed in the three fluidic lenses. Preferably, the control system includes (or is in communication with) a pump (not shown) which injects and withdraws fluid from a container (not shown). By injecting and withdrawing fluid from the lenses, high and low order aberrations are eliminated prior to the photography, since the fluidic lenses are capable of adjusting to the specific needs of the eye, in the same manner as described above.

Fundus camera 1402 is preferably equipped with white flush or a scanning laser ophthalmoscope or various lasers with different wavelengths from ultraviolet to infra-red wave length to obtain various visual information from the retina, choroid and optic nerve head. At low energy, the coagulative laser 1418 in FIG. 4 acts as an aiming beam, so it may be both coagulative and non-coagulative depending on its energy level. An Optical coherence tomography (OCT) 1416 or a laser can replace the scanning laser 1418 (or coagulative laser) to obtain two or three dimensional histological images from the eye structures or the laser can perform a precise coagulation of the retina along with the OCT images.

The fundus camera 1402 is also connected to a digital camera 1420 and/or a visualization monitor. Therefore, the images captured by the fundus camera can be viewed in real time or captured for viewing at a later time.

Additionally, the camera position can be moved into any desired position by a two way mirror that is positioned behind the fluidic lens.

The present system results in a compact, lightweight, precise and inexpensive advanced camera system eliminating the need for the complex prior technology which uses deformable mirrors.

Figure 5:
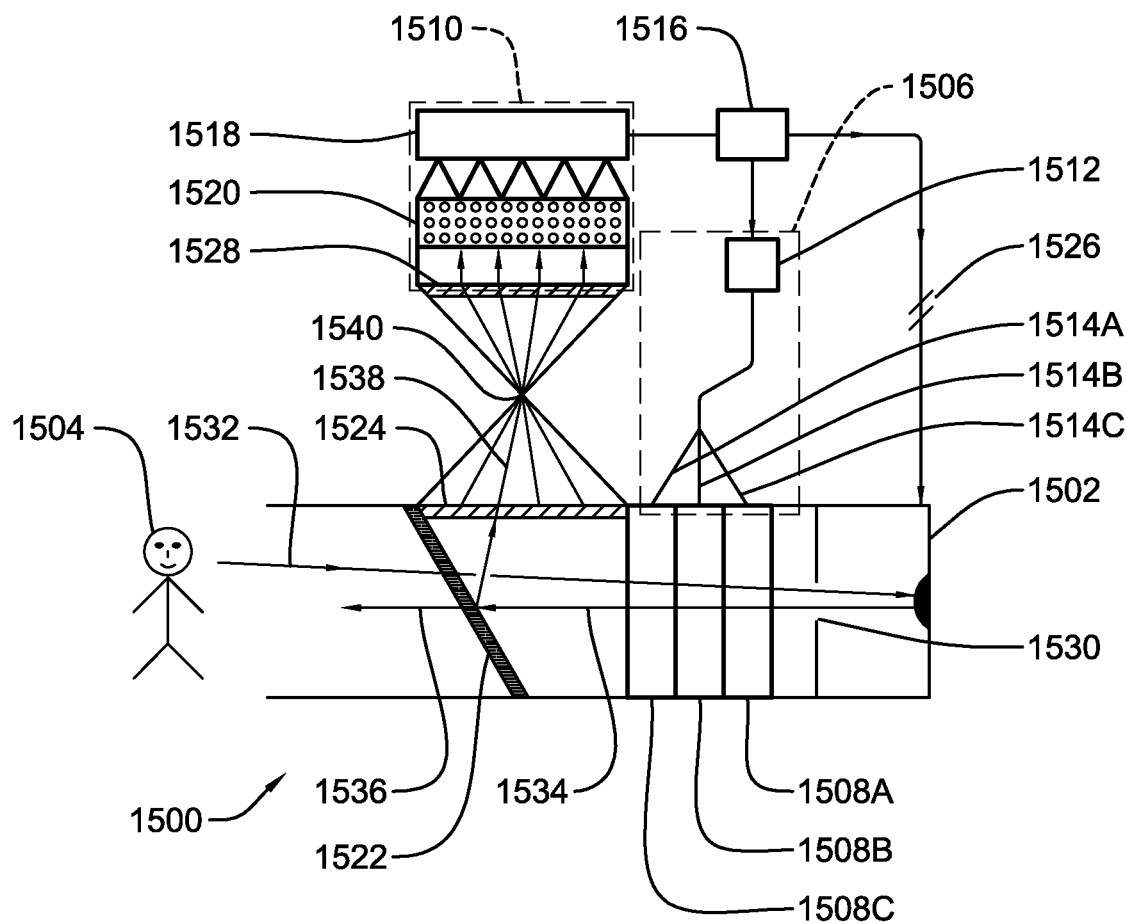
FIG. 5 illustrates yet another embodiment of the present invention in which an automated camera system is shown, wherein the automated camera system comprises a plurality of fluidic lenses.

FIG. 5 illustrates yet another embodiment of the present invention. In particular, FIG. 5 illustrates an automated camera system 1500, wherein the light waves entering a camera are corrected using a plurality of fluidic lenses 1508A, 1508B, and 1508C. As shown in FIG. 5, the automated camera system 1500 generally comprises a camera 1502 configured to capture an image of an object 1504; a plurality of fluidic lenses (e.g., three fluidic lenses 1508A, 1508B, and 1508C) disposed between the camera 1502 and the object 1504, each of the plurality of fluidic lenses 1508A, 1508B, and 1508C having a respective chamber that receives a fluid therein; a fluid control system 1506 operatively coupled to each of the plurality of fluidic lenses 1508A, 1508B, and 1508C, the fluid control system 1506 configured to insert an amount of the fluid into the respective chamber of each of the plurality of fluidic lenses 1508A, 1508B, and 1508C, or remove an amount of the fluid from the respective chamber of each of the plurality of fluidic lenses 1508A, 1508B, and 1508C, in order to change the shape of each of the plurality of fluidic lenses 1508A, 1508B, and 1508C in accordance with the amount of fluid therein; and a Shack-Hartmann sensor assembly 1510 operatively coupled to the fluid control system 1506, the Shack-Hartmann sensor assembly 1510 by means of the fluid control system 1506 configured to automatically control the amount of the fluid in the respective chamber of each of the plurality of fluidic lenses 1508A, 1508B, and 1508C, thereby automatically focusing the camera 1502 so that the image captured of the object 1504 is in focus. The camera 1502 may comprise any one of: (i) a digital camera for photography, (ii) a camera for automated microscopy, (iii) an optical coherence tomography (OCT) camera, (iv) a video surveillance camera, or (v) a camera for any other form of imaging, such as telesystem imager or a laser scanner, etc. The camera 1502 may record visible light images, infrared (IR) light images, ultraviolet (UV) light images, etc. Advantageously, the camera 1502 has no moving parts and is automatically focused by means of the plurality of fluidic lenses 1508A, 1508B, and 1508C.

As shown in FIG. 5, the camera 1502 comprises a camera aperture 1530 that allows light rays to pass therethrough. The camera 1502 may also comprise a standard lens that is disposed behind the plurality of fluidic lenses 1508A, 1508B, and 1508C.

In the automated camera system 1500 of FIG. 5, the three fluidic lenses may include a spherical lens 1508A, a first cylindrical lens 1508B, and a second cylindrical lens 1508C. In the illustrated embodiment, the spherical lens 1508A, which is closest to the camera 1502, may be a spherical lens as illustrated in FIG. 1. Similarly, in the illustrated embodiment, the first and second cylindrical lenses 1508B, 1508C, which are disposed in front the spherical lens 1508A, may each be a cylindrical lens as illustrated in FIG. 2. In an exemplary embodiment, the spherical lens 1508A is disposed in a first plane, the first cylindrical lens 1508B is disposed in a second plane, and the second cylindrical lens 1508C is disposed in a third plane. Each of the first, second, and third planes are oriented parallel or generally parallel to one another. Also, the first cylindrical lens 1508B has a first axis and the second cylindrical lens 1508C has a second axis. The first axis of the first cylindrical lens 1508B is disposed at an angle of approximately 45 degrees relative to the second axis of the second cylindrical lens 1508C. In addition, in an exemplary embodiment, the first plane of the spherical lens 1508A is disposed closer to the camera 1502 than the second plane of the first cylindrical lens 1508B and the third plane of the second cylindrical lens 1508C.

Referring again to the illustrative embodiment of FIG. 5, it can be seen that the fluid control system 1506 comprises a pump 1512 and a plurality of fluid distribution lines 1514A, 1514B, 1514C. Each of the plurality of fluid distribution lines 1514A, 1514B, 1514C fluidly connects the pump to a respective one of the plurality of fluidic lenses 1508A, 1508B, and 1508C. The pump 1512 adjusts the refractive power of the plurality of fluidic lenses 1508A, 1508B, and 1508C by inserting an amount of fluid into, or removing an amount of fluid from, each of the respective chambers of the plurality of fluidic lenses 1508A, 1508B, and 1508C.

With reference again to FIG. 5, it can be seen that the illustrative automated camera system 1500 further includes a data processing device 1516, which may be in the form of a personal computing device or personal computer. The data processing device 1516 (i.e., computer) of the automated camera system 1500 may comprise a microprocessor for processing data, memory (e.g., random access memory or RAM) for storing data during the processing thereof, and data storage device(s), such as one or more hard drives, compact disk drives, floppy disk drives, flash drives, or any combination thereof. At least one visual display device (i.e., monitor or display) may be operatively coupled to the data processing device 1516 (i.e., computer). Also, a plurality of user data input devices, such as a keyboard and a mouse, may be operatively coupled to the data processing device 1516 (i.e., computer) so that a user is able to enter data into the data processing device 1516.

As shown in FIG. 5, the data processing device 1516 (i.e., computer) is operatively connected to the pump 1512 of the fluid control system 1506 by, for example, a wired connection or a wireless connection. Also, the data processing device 1516 (i.e., computer) is operatively connected to the Shack-Hartmann sensor assembly 1510 by a wired connection or a wireless connection. The data processing device (i.e., computer) is specifically programmed to control the operation of the pump 1512 of the fluid control system 1506 based upon one or more output signals from the Shack-Hartmann sensor assembly 1510. Also, as shown in FIG. 5, the data processing device 1516 (i.e., computer) is operatively coupled to the camera 1502 by, for example, a wired connection or a wireless connection. When the Shack-Hartmann sensor assembly 1510 indicates to the data processing device 1516 (i.e., computer) that the object 1504 is in focus for the camera 1502, the data processing device 1516 is specially programmed to emit one or more initiation signals to the camera 1502 instructing the camera to capture the image of the object 1504. That is, the data processing device 1516 initiates a recording by the camera 1502 (e.g., a single photograph or a movie/video) or initiates an action, such as surveillance of an area with in-focus photos (i.e., if the camera 1502 is in the form of a video surveillance camera). As also shown in FIG. 5, an on-off switch 1526 may be provided to activate or deactivate the functionality of the automated camera system 1500 described herein. That is, when the on-off switch 1526 is in the "on" position, the data processing device 1516 automatically controls the operation of the camera 1502 by means of the one or more initiation signals that automatically initiate the capturing of the image (i.e., the automatic mode). Conversely, when the on-off switch 1526 is in the "off" position, the camera 1502 is in the non-automatic mode, whereby the operation of the camera 1502 is manually controlled by a user thereof (e.g., the user is required to manually focus the camera 1502 in the non-automatic mode).

In FIG. 5, it can be seen that the Shack-Hartmann sensor assembly 1510 comprises a charge-coupled device (CCD) array 1518 and a lenslet array 1520. The charge-coupled device (CCD) array 1518 of the Shack-Hartmann sensor assembly 1510 is operatively connected to the data processing device 1516 (i.e., computer) by, for example, a wired connection or a wireless connection. Also, as shown in FIG. 5, the automated camera system 1500 further includes a dichroic mirror 1522 disposed in front of the plurality of fluidic lenses 1508A, 1508B, and 1508C. The dichroic mirror 1522 is located between the plurality of fluidic lenses 1508A, 1508B, and 1508C and the lenslet array 1520 of Shack-Hartmann sensor assembly 1510 in the path of the light. The dichroic mirror 1522 allows the light rays 1532 from the external light source outside the automated camera system 1500 to pass therethrough (as indicated by arrow 1532 in FIG. 5). The external light source could be sunlight, an artificial flash light, or an external source that generates an infrared light. The external light source illuminates the object 1504 that is being photographed or recorded by the camera 1502. The automated camera system 1500 additionally includes a first diffractive lens 1524 or a holographic optical element (HOE) disposed between the dichroic mirror 1522 and the lenslet array 1520 in the path of the light. A holographic optical element (HOE) is essentially a diffractic element, but it is made with the technique of a hologram, which results in a very thin diffractive film. A holographic optical element (HOE) is easily reproducible and inexpensive to fabricate. The first diffractive lens 1524 or holographic optical element (HOE) directs the portion 1538 of the light that is reflected from the dichroic mirror 1522 to a single focal point 1540. After passing through the single focal point 1540, the reflected light passes through a second diffractive lens 1528 before entering the lenslet array 1520 of the Shack-Hartmann sensor assembly 1510. The first and second diffractive lens 1524, 1528 are required in the automated camera system 1500 in order to maintain the fidelity of the reflected light 1538. In order to avoid obscuring the image being captured by the camera 1502, the Shack-Hartmann sensor assembly 1510 must be located outside of the direct focal line of the camera 1502.

Now, with reference again to FIG. 5, the functionality of the automated camera system 1500 of FIG. 5 will be described. Initially, as explained above, the light rays 1532 from the external light source pass through dichroic mirror 1522 and the plurality of fluidic lenses 1508A, 1508B, and 1508C, and then, are reflected back from the camera 1502 (i.e., reflected light 1534 in FIG. 5). As shown in FIG. 5, the light waves or rays 1534 that are reflected back from the camera 1502 initially pass through the plurality of fluidic lenses 1508A, 1508B, and 1508C. In particular, the light waves pass through the spherical fluidic lens 1508A first, then followed by the first cylindrical fluidic lens 1508B, and finally the second cylindrical fluidic lens 1508C. After passing through the plurality of fluidic lenses 1508A, 1508B, and 1508C, a first portion 1536 of the reflected light 1534 passes back through the dichroic mirror 1522 to the outside, while a second portion 1538 of the reflected light 1534 is reflected by the dichroic mirror 1522 through the first diffractive lens 1524. As explained above, the first diffractive lens 1524 directs the second portion 1538 of the light that is reflected from the dichroic mirror 1522 to a single focal point 1540. After passing through the single focal point 1540, the reflected light 1538 passes through a second diffractive lens 1528 before entering the lenslet array 1520 of the Shack-Hartmann sensor assembly 1510. After the light waves are transmitted to the lenslet array 1520 of the Shack-Hartmann sensor assembly 1510, a light spotfield is created on the charge-coupled device (CCD) array or CCD camera 1518 of the Shack-Hartmann sensor assembly 1510 so that the intensity and location of each light spot in the spotfield may be determined. When light spots in the spotfield are crisp and clear in the Shack-Hartmann sensor assembly 1510, they are in focus. Conversely, when light spots in the spotfield are fuzzy in the Shack-Hartmann sensor assembly 1510, they are not in focus. When all of the light spots in the spotfield are in focus, the subject of the photography (i.e., object 1504) is in focus for the camera 1502. Upon determining the intensity and location information from the spotfield, the Shack-Hartmann sensor assembly 1510, by means of the data processing device 1516, controls the refractive power of the lenses 1508A, 1508B, and 1508C through the computerized fluid pump 1512 connected to the fluidic lenses 1508A, 1508B, and 1508C. When the Shack-Hartmann sensor assembly 1510 indicates that the object 1504 of view (a landscape, person, etc.) is in focus for the camera 1502, the data processing device 1516 is specially programmed to emit one or more initiation signals to the camera 1502 so as to initiate the recording of a photo or video, with a flash or without a flash light using infra-red light.

Figure 8:
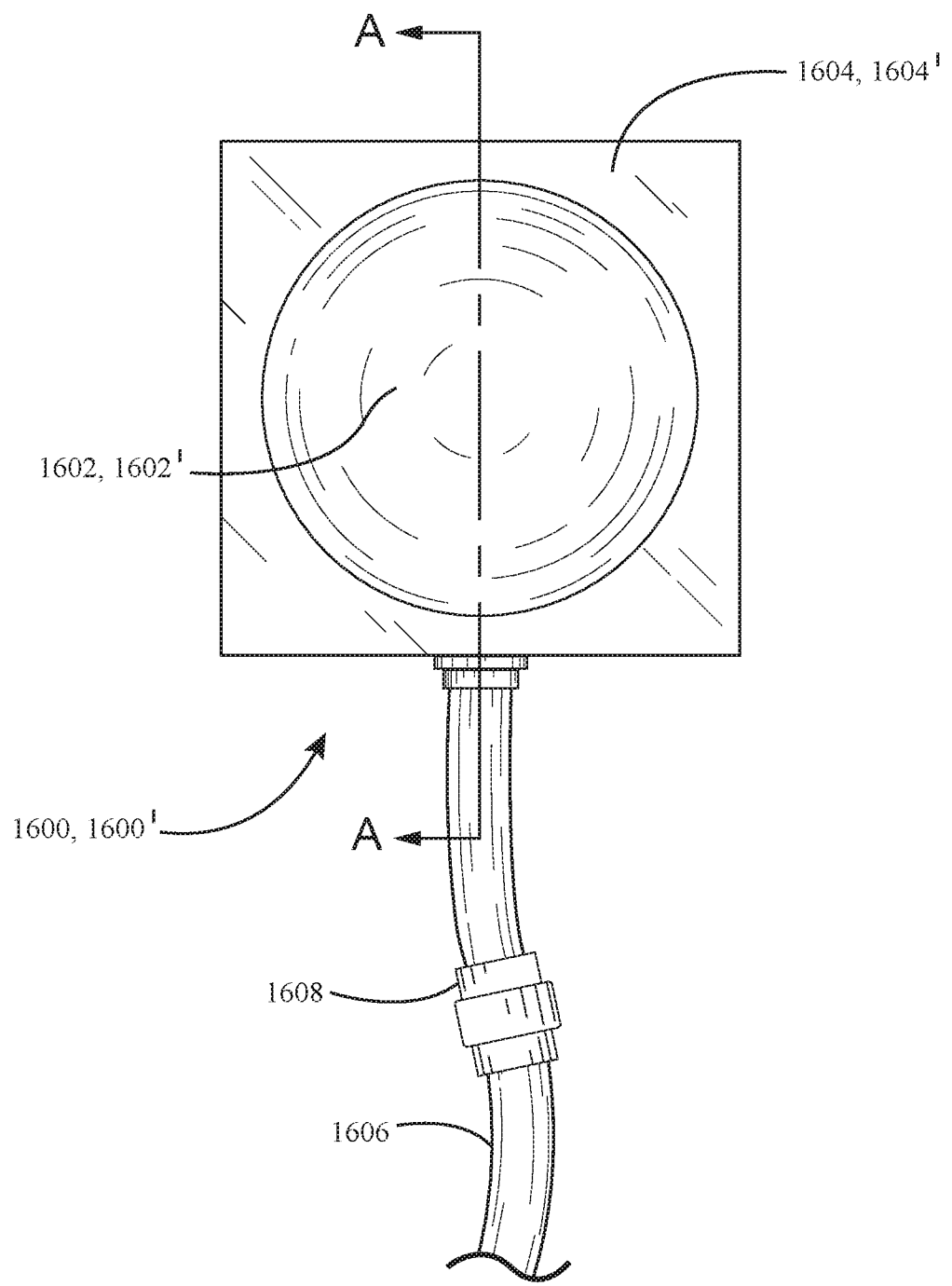
FIG. 8 is a front/top view of the convex, flexible fluidic mirrors of FIGS. 6 and 7.

FIGS. 6-17 illustrate additional embodiments of the present invention. In accordance with a first set of illustrative embodiments, a flexible fluidic mirror will be described with reference to FIGS. 6-13. The flexible fluidic mirror generally comprises a flexible membrane defining a fluid chamber, and an outer housing supporting the flexible fluid membrane. The surface of the flexible membrane of the fluidic mirror may be coated with nanoparticles that reflect light back so as to create the necessary mirror effect. The flexible membrane of the fluidic mirror may be disposed in either a convex orientation or in a concave orientation depending on whether fluid is being injected into, or withdrawn from the fluid chamber or cavity. As shown in FIG. 6, the biconvex, flexible fluidic mirror 1600 comprises a flexible membrane 1602 that is convex on both sides of the mirror. The flexible membrane 1602 is supported in an outer housing 1604, and the flexible membrane 1602 and the outer housing 1604 defines an internal fluid chamber 1610 for receiving a fluid therein. A fluid pipe or tube 1606 is fluidly coupled to the fluid chamber 1610 of the fluidic mirror 1600 so that the fluid may be injected into, or withdrawn from the fluid chamber 1610 by means of a fluid pump (e.g., the fluid pump 1512 depicted in FIG. 5) may be fluidly connected to the fluid pipe 1606). Also, referring again to FIG. 6, it can be seen that the fluid pipe or tube 1606 comprises a valve 1608 disposed therein to selectively regulate the fluid flow through the fluid pipe 1606 (i.e., turn the fluid flow on or off). In FIG. 6, it can be seen that light rays 1612 are shown striking the front surface of the mirror 1600, and reflecting off the front surface of the mirror 1600. A front view (top view) of the fluidic mirror of FIG. 6 is shown in FIG. 8. As shown in FIG. 8, the outer housing 1604 of the mirror 1600 forms a circular restriction that houses the flexible membrane 1602 therein.

The flexible fluidic mirror 1600' depicted in FIG. 7 is similar to that shown in FIG. 6, except that the flexible membrane 1602' has only a single convex front portion, rather than the biconvex configuration of FIG. 6. As shown in FIG. 7, the outer housing 1604' of the mirror 1600' has a solid, rigid back portion 1604$a'$ that does not deform as a result of fluid pressure exerted thereon. Also, similar to the embodiment of FIG. 6, the outer housing 1604' additionally comprises a solid, rigid peripheral side housing 1604$b'$. In FIG. 7, it can be seen that, when the incoming light beam 1614 strikes the convex mirror 1600', the light is reflected by the front surface of the mirror 1600' (as indicated by reflected light beams 1616). One or more of the reflected light beams 1616 may be transmitted via a dichroic mirror (e.g., the dichroic mirror 1522 in FIG. 5) to a diffractive lens or a holographic element (e.g., the diffractive lens 1524, 1528 in FIG. 5) to a Shack-Hartmann system (e.g., the Shack-Hartmann assembly 1510 in FIG. 5) to increase or decrease the amount of the fluid in the mirror cavity 1610' by a processing device (e.g., a computer or computing device with a microprocessor, such as the data processing device 1516 in FIG. 5) until the beam is in focus.

Figure 11:
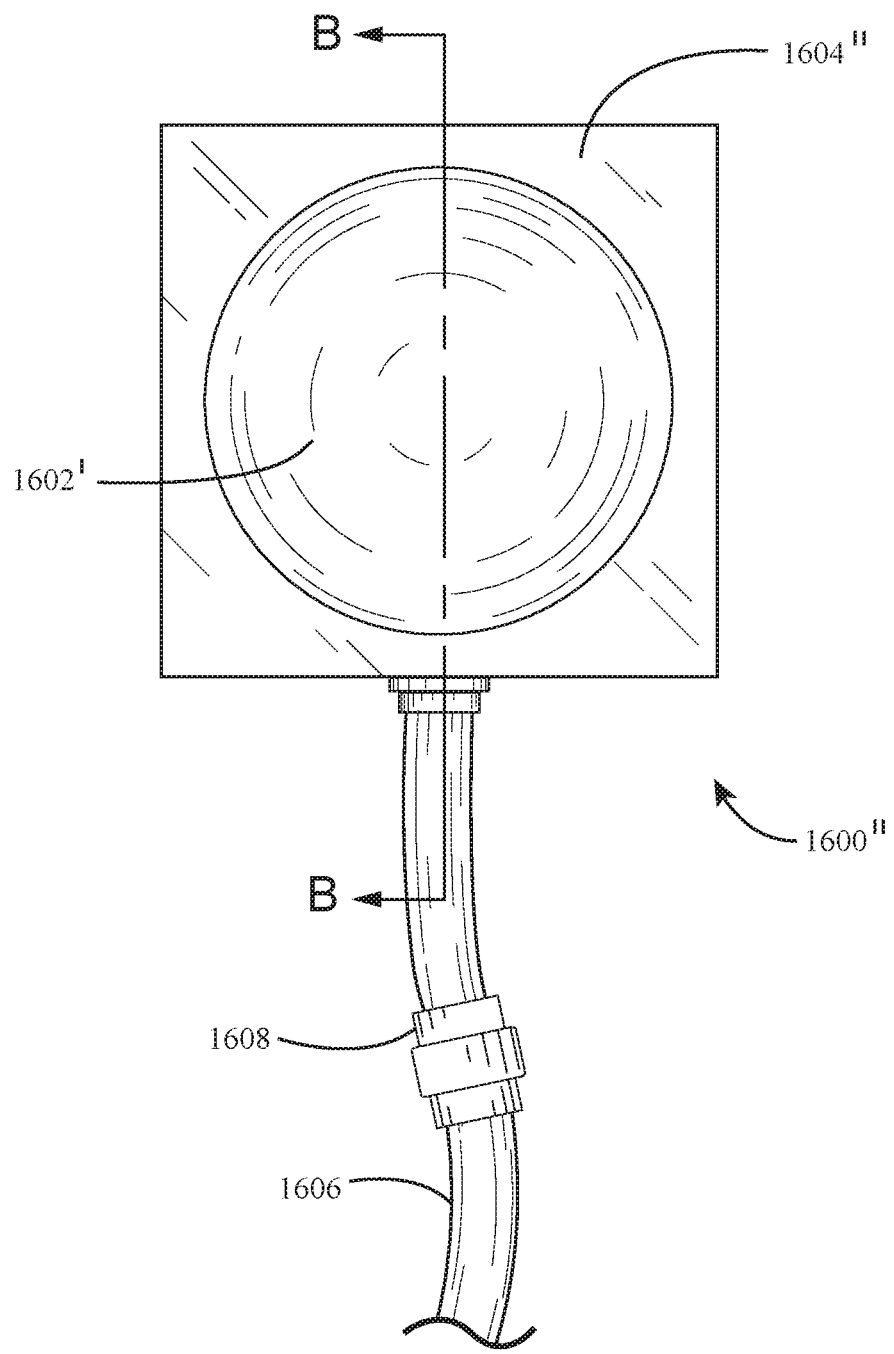
FIG. 11 is a front/top view of the flexible concave fluidic mirrors of FIGS. 9 and 10.

The circular flexible fluidic mirror 1600" depicted in FIGS. 9-11 is similar to that described above with regard to FIGS. 6 and 7, except that the flexible membrane 1602' is configured to be deformed into a concave configuration, rather than the convex configurations of FIGS. 6 and 7. As shown in the side sectional views of FIGS. 9 and 10, the outer housing 1604" of the mirror 1600" has a solid or semi-solid back portion 1604$a"$ and a solid, rigid peripheral side housing 1604$b"$. In FIG. 9, the flexible membrane 1602' is shown in its relaxed state, and fluid is neither flowing out of, nor into the fluid chamber 1610' of the mirror 1600". Although, in FIG. 10, fluid is depicted flowing out of the fluid chamber 1610' of the mirror 1600" through the fluid pipe 1606 in order to create the concave configuration of the mirror 1600". As shown in FIGS. 10 and 11, the solid or semi-solid back portion 1604$a"$ of the mirror outer housing 1604" may be convexly-shaped in order to accommodate the concave deformation of the front flexible membrane 1602'. A front view (top view) of the fluidic mirror of FIGS. 9 and 10 is shown in FIG. 11. As shown in FIG. 11, the outer housing 1604" of the mirror 1600" forms a circular restriction that houses the flexible membrane 1602' therein.

Figure 12:
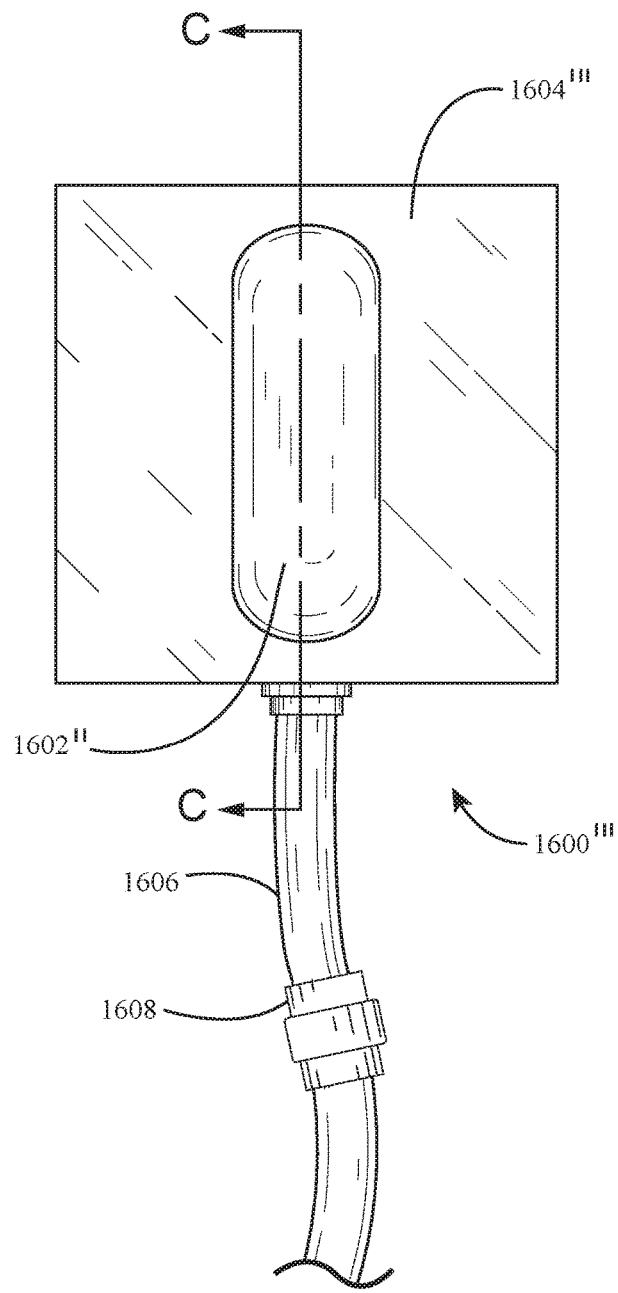
FIG. 12 is a front/top view of a flexible parabolic or elliptical fluidic mirror, according to still another embodiment of the invention.
Figure 13:
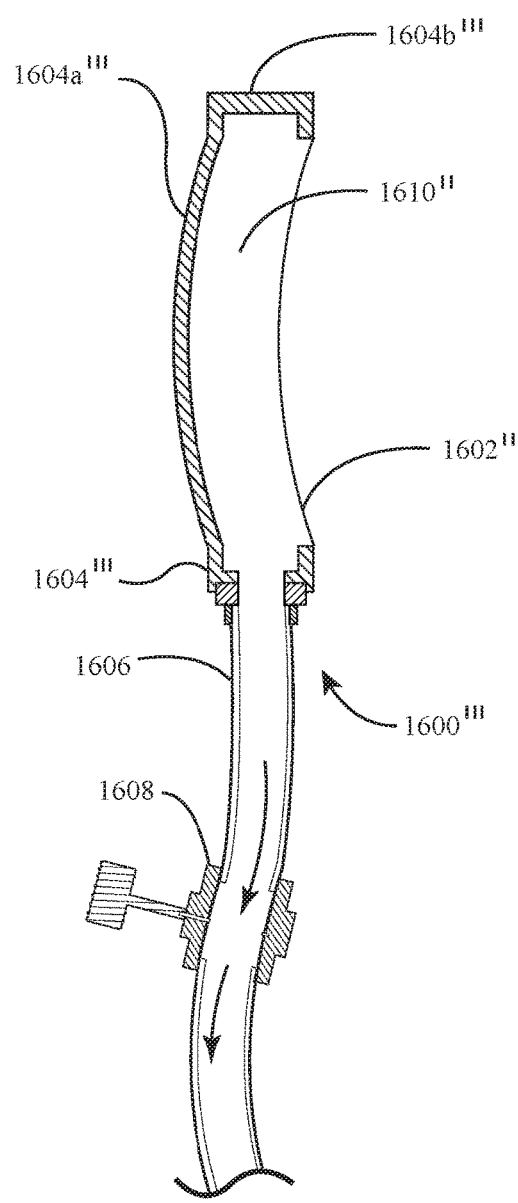
FIG. 13 is a side sectional view of the flexible parabolic or elliptical fluidic mirror of FIG. 12, wherein the section is generally cut along the cutting-plane line C-C in FIG. 12.

A flexible parabolic or elliptical mirror 1600''' is depicted in FIGS. 12 and 13. As shown in the sectional side view of FIG. 13, the flexible fluidic mirror 1600''' comprises a flexible membrane 1602" that has a concave configuration (i.e., similar to the circular mirror 1600" described above with respect to FIG. 10). Also, similar to the mirrors 1600, 1600', 1600" described above, the flexible membrane 1602" is supported in an outer housing 1604''', and the flexible membrane 1602" defines an internal fluid chamber 1610" for receiving a fluid therein. Like the mirror 1600" of FIGS. 9-11, the outer housing 1604''' of the mirror 1600''' comprises a convexly-shaped solid, rigid back portion 1604$a'$ and a solid, rigid peripheral side housing 1604$b'''$. In FIG. 13, fluid is depicted flowing out of the mirror 1600' through the fluid pipe 1606, which is fluidly coupled to the flexible membrane 1602", in order to create the concave/convex configuration of the mirror 1600'. Fluid may be injected into, or withdrawn from the fluid chamber 1610" of the mirror flexible membrane 1602" via the fluid pipe 1606, which is fluidly coupled to a fluid pump system (e.g., the fluid pump 1512 depicted in FIG. 5 may be fluidly connected to the fluid pipe 1606). A front view (top view) of the fluidic mirror of FIG. 13 is shown in FIG. 12. As shown in FIG. 12, the outer housing 1604''' of the mirror 1600''' forms an elliptical or oval-shaped restriction that houses the flexible membrane 1602" therein.

The surfaces of the flexible membranes 1602, 1602', 1602" of the illustrative mirrors 1600, 1600', 1600", 1600''' described above may be sprayed or coated with reflective nanoparticles that are capable of reflecting back the incoming light, such as nanoparticles of silver, iron, aluminum, zinc, gold, or another suitable metallic substance. Also, the surfaces of the flexible membranes 1602, 1602', 1602" may be sprayed, coated, or covered with a synthetic flexible reflective film to reflect the incoming light.

In one or more embodiments, the reflective coating or film disposed on the flexible membrane 1602, 1602', 1602" of the illustrative mirrors 1600, 1600', 1600", 1600''' may comprise reflective nanoparticles painted on the flexible membrane or sprayed on the flexible membrane after a polymerizable substance is cured and a desired concave or convex shape of the flexible fluidic mirror is achieved (as will be described hereinafter).

The illustrative embodiments of FIGS. 6-11 depict the manner in which a fluidic pump system may be used to modify the configurations of the flexible membranes 1602, 1602' of the circular mirrors 1600, 1600', 1600" so as to form a variety of different convex and concave configurations. The illustrative embodiment of FIGS. 12 and 13 depicts the manner in which a fluidic pump system also may be used to modify the configuration of the flexible membrane 1602" of an elliptical or parabolic mirror 1600'''.

In the embodiments of FIGS. 6-13, the mirror aspect of the lens is generally limited to the front surface of the flexible membranes 1602, 1602', 1602". As such, the transparency of the back surface of the flexible membranes 1602, 1602', 1602" is generally unimportant. However, the size of the fluid chambers 1610, 1610', 1610" of the mirror flexible membranes 1602, 1602', 1602" affects the ability to move the membranes 1602, 1602', 1602" from a high convexity to a high concavity position.

In one or more embodiments, the fluid disposed in the chambers 1610, 1610', 1610" of the flexible membranes 1602, 1602', 1602" of the fluidic mirrors 1600, 1600', 1600", 1600' is in the form of a polymerizable substance so that the substance is capable of being cured after the fluidic mirrors 1600, 1600', 1600", 1600''' are formed into a desired concave or convex shape. That is, after a desired deformation of the surface of the flexible membrane 1602, 1602', 1602" by means of fluid insertion or withdrawal, the polymerizable substance in the fluid cavity 1610, 1610', 1610" may be hardened or cured so that a desired mirror shape is created. In one embodiment, the polymerizable substance (e.g., a silicone oil) disposed in the chamber of the flexible fluidic mirror may be cured by the application of at least one of: (i) ultraviolet radiation, and (ii) microwaves. In another embodiment, the polymerizable substance disposed in the chamber 1610, 1610', 1610" of the fluidic mirror 1600, 1600', 1600", 1600' may comprise an initial liquid polymer and a chemical crosslinker initiator. In this embodiment, the fluidic mirror 1600, 1600', 1600", 1600''' is fixed into the desired concave or convex shape by mixing the initial liquid polymer with the chemical crosslinker initiator so as to solidify the flexible membrane 1602, 1602', 1602" and achieve the desired curvature (i.e., to harden and fix the desired curvature).

In contrast to the fluidic mirror 1600, 1600', 1600", 1600''' described above, the hybrid flexible fluidic lens that will be described hereinafter requires the fluid in the fluidic chamber of the lens to remain a liquid so that the hybrid flexible fluidic lens remains adjustable using the two different options of either fluidic adjustment or adjustment by an electromagnetic actuator. Also, as will be described hereinafter, both the front and back surfaces of the hybrid flexible fluidic lens are clear or transparent in order to allow light to pass therethrough.

In accordance with a second set of illustrative embodiments, a hybrid system that utilizes both a fluidic pump and an electrically induced magnet will be described with reference to FIGS. 14-17. A hybrid, flexible concave/convex mirror or lens is depicted in the embodiments of FIGS. 14-17. In general, in these illustrative embodiments, the control of the membrane deflection of the flexible concave/convex mirror or lens is capable of being done by two mechanisms. First of all, injection or withdrawal of the fluid from the fluid chamber of the mirror or lens is done using an electric fluid pump that is fluidly coupled to the fluid chamber of the mirror or lens via a fluid pipe or tube (e.g., the fluid pump 1512 depicted in FIG. 5 may be fluidly connected to the fluid pipe of the mirror or lens). The injection of fluid into the chamber creates a membrane with a convex surface, while the withdrawal of fluid from the chamber creates a membrane with a concave surface. Secondly, the front portion of the flexible membrane also may be under the control of a magnetic plate and actuator. Both the fluid-based and magnetic mechanisms are used by activating a sensor and a processor to achieve the desired dioptic power. The magnetic plate is capable of making the front surface of the mirror or lens membrane convex, but it is not capable of making it concave. As such, the fluidic pump system is needed to withdraw the fluid from the lens or mirror to create a concave surface. As will be described in more detail hereinafter, the motion of the frontal magnetic plate is controlled by the magnetic force generated by the electromagnetic located on the back surface of the flexible membrane or outer housing.

Advantageously, the magnetic system of the hybrid lens or mirror enables a fast refinement or adjustment of the mirror or lens. During this quick adjustment of the mirror or lens, the convexity of the flexible mirror or lens is controlled by a magnetic field generated by the magnetic system, while the valve member of the fluidic outflow tube is closed so as to prevent fluid flow through the tube. Then, an electric potential is applied to the solid plate behind the mirror or lens. By electrically increasing the magnetic field, the thin ferromagnetic plate attached on the front surface of the membrane moves backward, thus increasing the pressure in the fluidic lens. This magnetic force increases the pressure inside the mirror lens, which in turn, pushes the flexible membrane at the center of the mirror or lens forward so as to create a more convex central portion of the mirror or lens. By decreasing the magnetic field, the frontal thin magnetic plate is released, which in turn, reduces the fluidic pressure or force in the mirror or lens, and the flexible membrane of the mirror or lens retreats backwards, thereby decreasing the convexity of the flexible membrane (see e.g., FIG. 15).

Now, turning to FIGS. 14-17, the illustrative embodiments of the hybrid mirror (or lens if the membrane is not provided with a reflective coating) will be described. Initially, as shown in the side sectional view of FIG. 15, the hybrid mirror 1700 comprises a flexible membrane 1702 that is convex on the front side of the mirror. The flexible membrane 1702 of the hybrid mirror 1700 is supported in an outer housing 1704, and the flexible membrane 1702 and outer housing 1704 defines an internal fluid chamber 1710 for receiving a fluid therein. As shown in FIG. 15, the back side of the hybrid mirror 1700 may comprise a solid or semi-solid transparent back portion 1716 (e.g., a transparent pane of glass) that does not deform as a result of fluid pressure exerted thereon. A fluid pipe or tube 1706 is fluidly coupled to the fluid chamber 1710 of the fluidic mirror 1700 so that the fluid may be injected into, or withdrawn from the fluid chamber 1710 by means of a fluid pump (e.g., the fluid pump 1512 depicted in FIG. 5 may be fluidly connected to the fluid pipe 1706). Also, referring again to FIG. 15, it can be seen that the fluid pipe or tube 1706 comprises a valve 1708 disposed therein to selectively regulate the fluid flow through the fluid pipe 1706 (i.e., turn the fluid flow on or off). In addition, as illustrated in FIG. 15, a ferromagnetic annular plate 1712 is provided on the front surface of the flexible membrane 1702 for altering the shape of the front portion of the flexible membrane 1702 (i.e., by making the front portion of the flexible membrane 1702 more or less convex in shape). An electromagnetic annular plate 1714 is provided on the back panel 1716 of the hybrid mirror 1700 that selectively attracts or repels the ferromagnetic annular plate 1712 on the front surface of the flexible membrane 1702 to make the flexible membrane 1702 more convex or less convex. The magnetic force (as diagrammatically represented by the magnetic flux lines 1718 in FIG. 15) exerted by the electromagnetic back plate 1714 on the ferromagnetic front plate 1712 is selectively controlled by regulating the electrical current flow to the electromagnetic annular plate 1714. In the embodiment of FIG. 15, the fluid valve 1708 is shown in its closed position so that fine adjustments may be made to the convexity of the flexible membrane 1702 by the magnetic system 1712, 1714.

As shown in FIG. 14, the outer housing 1704 of the hybrid mirror 1700 forms a circular restriction that houses the flexible membrane 1702 therein. Also, referring to FIG. 14, it can be seen that the ferromagnetic annular plate or ring 1712 is attached to the front surface of the flexible membrane 1702 to regulate the convexity of the flexible membrane 1702. In one embodiment of FIGS. 14 and 15, the front surface of the flexible membrane 1702 is provided with a reflective surface coating so that the flexible membrane 1702 functions as a mirror. Although, in one or more alternative embodiments of FIGS. 14 and 15, the reflective surface coating may be omitted from the flexible membrane 1702, and the flexible membrane 1702 may be transparent instead so that the flexible membrane 1702 functions as a lens. When the flexible membrane 1702 functions as a lens, the transparent back portion 1716 of the housing 1704 allows light rays to pass through the back wall of the housing 1704.

Figure 17:
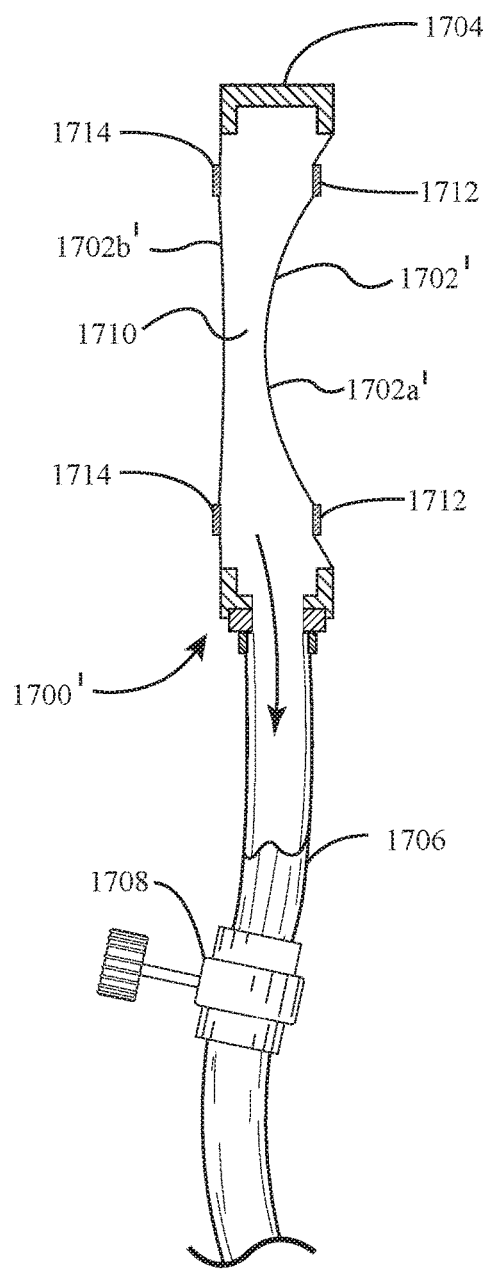
FIG. 17 is a side sectional view of another hybrid flexible fluidic mirror, according to yet another embodiment of the invention.

The circular hybrid mirror 1700' depicted in FIG. 17 is similar to that described above with regard to FIGS. 14 and 15, except that the flexible membrane 1702' has a concave front portion 1702a', rather than the convex configuration of FIGS. 14 and 15. Also, unlike the hybrid mirror 1700 of FIGS. 14 and 15, the hybrid mirror 1700' of FIG. 17 is additionally provided with a flexible rear membrane portion 1702b'. Similar to the hybrid mirror 1700 of FIGS. 14 and 15, the hybrid mirror 1700' comprises a magnetic adjustment system with a ferromagnetic annular plate or ring 1712 attached to the front surface of the front flexible membrane 1702a' and an electromagnetic annular plate 1714 attached to the back surface of the flexible rear membrane portion 1702b'. In FIG. 17, fluid is depicted flowing out of the fluid chamber 1710 of the mirror 1700' through the fluid pipe 1706 in order to create the concave configuration of the mirror 1700'.

Figure 16:
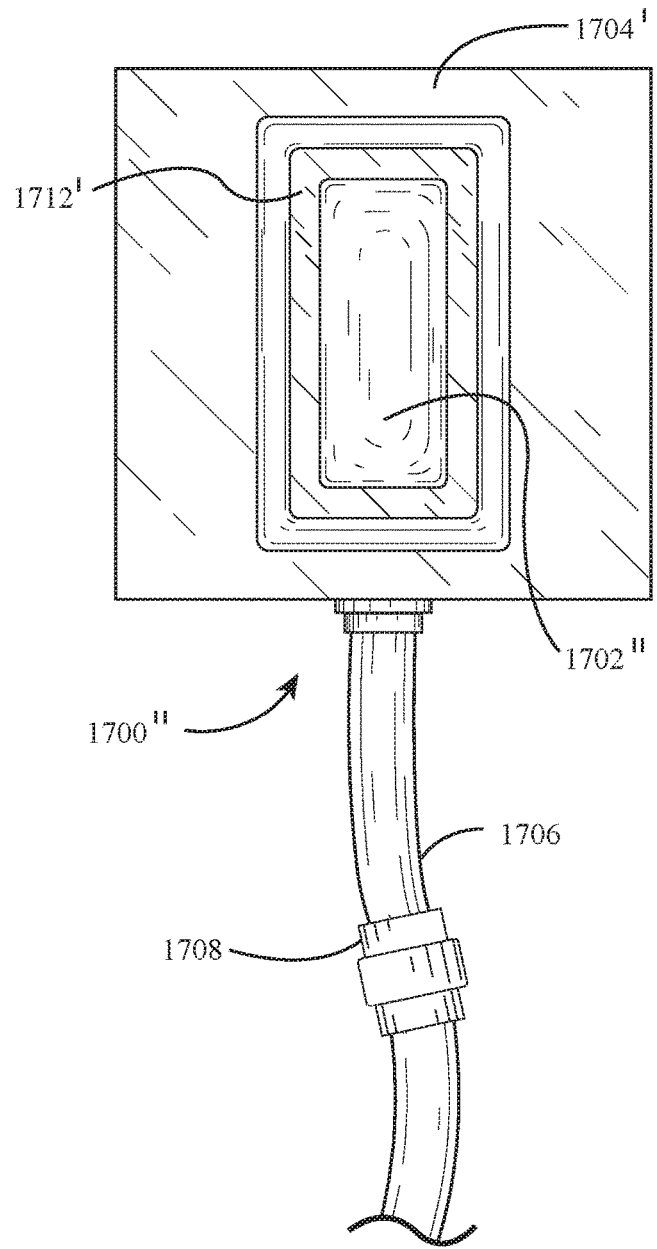
FIG. 16 is a front/top view of another hybrid flexible fluidic mirror, according to still another embodiment of the invention.

A front view (top view) of an alternative hybrid parabolic or elliptical mirror 1700" is depicted in FIG. 16. As shown in FIG. 16, the hybrid parabolic or elliptical mirror 1700" comprises an outer housing 1704' that forms a rectangular restriction that houses the flexible membrane 1702" therein. In addition, as depicted in FIG. 16, the hybrid parabolic or elliptical mirror 1700" comprises a ferromagnetic rectangular plate 1712' attached to the front surface of the flexible membrane 1702". A corresponding electromagnetic rectangular plate is provided on the back side of the housing 1704' that selectively attracts or repels the ferromagnetic rectangular plate 1712' on the front surface of the flexible membrane 1702" to make the flexible membrane 1702" more convex or less convex.

In one or more embodiments, if the flexible membrane is made flexible and transparent and the center of the back plate of the housing is also transparent (e.g., as shown in FIG. 15), the hybrid lens may also function as a refractive lens, a spherical fluidic lens, or astigmatic fluidic lens. Alternatively, if the flexible membrane is coated with reflective nanoparticles (as described above with respect to the flexible fluidic mirror of FIGS. 6-13), the hybrid system may be used as a mirror system.

In the illustrative embodiments of FIGS. 14-17, the entire hybrid mirror or lens control system, which includes the fluidic pump (e.g., pump 1512 in FIG. 5) and the electromagnet that generates the magnetic field, is under control of a sensor (e.g., Shack-Hartmann sensor assembly 1510, as shown in FIG. 5), which is connected to the fluidic mirrors or lenses via a specially programmed computer (e.g., the data processing device 1516 depicted in FIG. 5) that focuses the images properly for the functions as described above. The operator may also manually take over the control of the lenses if used in glasses or in a camera, etc.

The hybrid system of FIGS. 14-17 combines a fluid-based mirror or lens system with an electromagnetic force-based system that compresses the membrane of the mirror or lens for making fine adjustments thereto. The fluid injection and withdrawal ability of the hybrid system enables the fluidic lenses to assume either a convex surface (i.e., to operate as a plus lens) or a concave surface (i.e., to operate as a minus lens).

In one or more embodiments, the fluidic portion of the system may provide corrections ranging from −30.00 diopters (D) to +30.00 diopters (D), or more diopters (D) power at a step of 0.1 diopters (D), while the compressive part may add further adjustability to the system by adding small step corrections of 0.001 diopters (D), all under the control of the Shack-Hartmann system (e.g., Shack-Hartmann system 1510 in FIG. 5). Thus, this system provides an extremely high resolution that conventional solid lenses cannot achieve. Presently, conventional solid lenses are capable of correcting the refractive power from −0.25 D to +0.25 D.

In one or more embodiments, the refractive power of the fluidic lenses are uniformly controlled by the Shack-Hartmann sensor as a result of the fluidic pump injecting or withdrawing the fluid from the lens chambers via a processor (i.e., a computing device with a microprocessor).

In one or more other embodiments, the control of the refractive power of the lenses is performed with a hybrid lens system and a Shack-Hartmann sensor by: (a) injecting or withdrawing of fluid in some lenses, and (b) in the remaining lenses of the system, using a compressive ring-shaped magnetic plate 1712 (e.g., see FIG. 14) or rectangular frame shaped magnetic plate 1712' (e.g., see FIG. 16) located on the front (or alternatively on the back surface) of the fluidic lens. The compressive ring-shaped magnetic plate 1712 or the rectangular frame shaped magnetic plate 1712' may be moved forward or backward by an electromagnet located in the frame or the fluidic lens, like a solenoid. When the magnet is activated, it attracts the magnetic ring 1712 or the rectangular plate 1712', thereby compressing the internal lens fluid without causing the internal lens fluid to escape. The compression of the internal lens fluid forces the center of the lens membrane forward, thus making the curvature of the lens surface more or less convex, depending on the amount of force generated by the electromagnet. This force produces either a more convex spherical surface if the plate is ring-shaped or a more cylindrical lens if the restrictive plate is rectangular shaped.

In another embodiment, two (2) cylindrical lenses positioned forty-five (45) degrees from each other are activated with an electromagnetic force to compensate for astigmatic correction, while the spherical lens remains as a non-hybrid fluidic lens. The magnetically controlled cylindrical lenses, which perform correct cylindrical correction, together with the non-hybrid fluid spherical lens provides a complete hybrid combination lenses system and has the ability to provide collectively a refractive power of plus cylinder of 0.1-+10 D and a spherical correction of −30 D to +25 D or more diopters at any axis controlled by the Shack-Hartmann sensor through a processor (i.e., a computing device with a microprocessor).

This hybrid combination system, controlled by a sensor such as a Shack-Hartmann sensor, provides an automated camera which maintains the object in the focal plane at all times, regardless of the status of the object (i.e., whether it is still or in motion).

Other applications of the hybrid system may be used in a digital automatic recording camera, an endoscope, a surveillance camera, a motion picture camera, a military or a sport rifle, a remote controlled robotic system, an operating microscope, a perimetry unit used for evaluation of the visual field, a laboratory microscope, a lensometer, a system of two photon or multiphoton microscopy, confocal microscopy, optical coherence tomography (OCT), astronomical telescopes, etc. The hybrid system may also be used in other systems that are familiar in the art.

In one or more embodiments, the aforedescribed mirror (i.e., mirror 1600 or hybrid mirror 1700) may be equipped with a sensor that is capable of controlling the focal point of the fluidic mirror via a processor. The sensor may be a laser beam measuring the distance from an object to the mirror, the sensor may be a Shack-Hartmann sensor, or other means known in the art to focus and sharpen the image obtained by a telescope or focus the image on the object, such as in ophthalmic photography, or laser use in an elliptical mirror for the ophthalmology, etc.

It is readily apparent that the aforedescribed flexible fluidic mirror and hybrid system offer numerous advantages. First, the flexible fluidic mirror, which may be used as a concave mirror by adjusting the fluid amount therein, is generally easy and inexpensive to produce. In addition, the fluidic concave, elliptical, and parabolic mirrors described above are capable of being readily adjusted when needed, without requiring expensive movable parts. In particular, the refractive power of the surfaces of the inventive flexible fluidic mirrors described herein are capable of being easily adjusted so that the systems in which the fluidic mirrors are incorporated may be automated, and the images acquired by the systems may be automatically in focus when under the control of a sensor. Advantageously, the aforedescribed flexible fluidic mirrors may be easily produced for a wide variety of different applications, such as automobile industry side mirrors and telescope mirrors. Because these mirrors are easily adjustable, they are capable of being used to track a fast moving object. These mirrors also may be used for still photography, and for video applications. As described above, because the concave fluidic mirrors may also be elliptical or parabolic (e.g., see FIG. 12), they also may be effectively used in wide angle photography, optical coherence tomography (OCT), angiography, etc. Also, the aforedescribed flexible fluidic mirrors may be utilized in ophthalmology for visualization, photography or laser treatment of retina, lens, or cornea lesions located on a surface area, etc. The flexible fluidic mirrors are also useful in remote laser systems, such as the remote laser-imaging systems described in U.S. Pat. Nos. 8,452,372, 8,903,468 and 9,037,217, the disclosures of each of which are incorporated by reference herein in their entireties. For example, the solid, non-flexible elliptical mirror 220 in the wide angle camera of the remote laser-imaging systems described in U.S. Pat. Nos. 8,452,372, 8,903,468 and 9,037,217, may be replaced with the flexible fluidic mirror described herein.

In addition, the fluidic mirrors 1600, 1700 described herein may be used in other applications requiring concave surfaces in ophthalmology that conventionally employ fixed surfaces, such as in corneal topography equipment used for external imaging, or for three dimensional (3D) eye imaging devices that use rotating cameras. The mirrors in this type of equipment are used for doing perimetry to evaluate the visual field of a patient, or for doing electrophysiolgic evaluation of the retina (ERG) electroretinogram, or visual evoked potential (VEP) for evaluation of the function of the retina, optic nerve and the occipital brain cortex, in numerous diseases including traumatic brain injuries (TBIs), Alzheimer's disease, etc.

Next, turning to FIGS. 18a-18c and 19-21, the illustrative embodiments of the fluidic light field camera will be described. As will be described hereinafter, the digital light field photography (DLFP) camera includes microlenses that capture the information about the direction of the incoming light rays and a photosensor array that is disposed behind the microlenses. A specially programmed data processing device (e.g., a computer) is used to process the information obtained from the light field camera.

In one or more embodiments, the light field digital camera or digital light field photography (DIFLFP) camera comprises one or more fluidic optical element(s) as the objective lens providing a variable field of view for the camera. In one embodiment, a series of microlenses may be located at the focal point of the objective lens in a flat plane perpendicular to the axial rays of the objective lens. These microlenses separate the incoming rays of light entering the camera into individual small bundles. The individual small bundles of light are refracted on a series of light sensitive sensors that measure in hundreds of megapixels, which are located behind the plane of the microlenses, thereby converting the light energy into electrical signals. The electronically generated signals convey information regarding the direction of each light ray, view, and the intensity of each light ray to a processor or a computer. Each microlens has some overlapping view and perspective from the next one which can be retraced by an algorithm.

In one or more embodiments, the light sensitive sensors behind the lenslets of the camera record the incoming light and forward it as electrical signals to the camera's processor and act as an on/off switch for the camera's processor measuring the intensity of the light through its neuronal network and its algorithm to record changes in light intensity, while recording any motion or dynamic displacement of an object or part of an object in front of the camera in a nanosecond to a microsecond of time. The processor of the camera with its neuronal network algorithm processes the images as the retina and brain in a human being functions by finding the pattern in the data and its dynamic changes of the image and its trend over a very short period of time (e.g., nanosecond). The information is stored in the memory system of the camera's processor, as known in the art, as memory resistor (memristor) relating to electric charge and magnetic flux linkage, which can be retrieved immediately or later, and further analyzed by mathematical algorithms of the camera.

In one or more embodiments, the light field camera may have either a tunable lens or a fluidic lens that will be described hereinafter. If a tunable lens is utilized, the tunable lens may be in the form of a shape-changing polymer lens (e.g., an Optotune® lens), a liquid crystal lens, an electrically tunable lens (e.g., using electrowetting, such as a Varioptic® lens). Alternatively, the preferred fluidic lens, which affords a wide range of adjustability with a simple membrane structure, described hereinafter may be used in the light field camera.

Figure 18C:
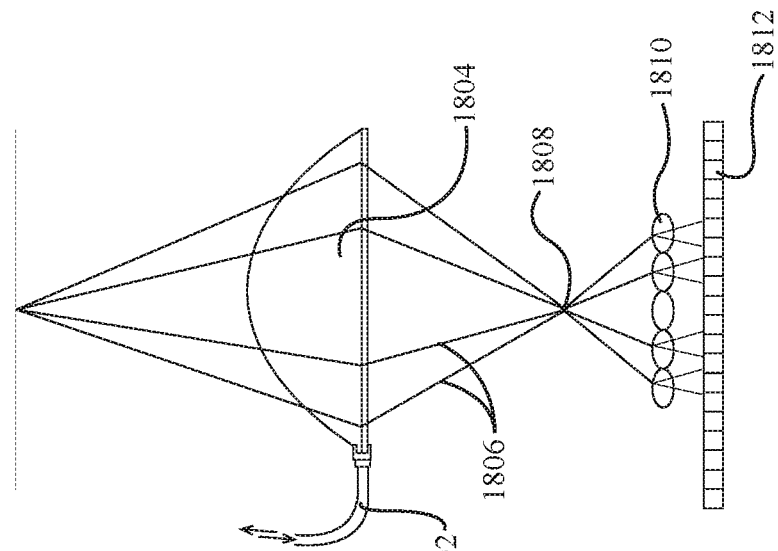
FIG. 18c is yet another diagrammatic representation of the fluidic digital light field photography (DIFLFP) camera described herein, wherein the image of the object is being focused in front of the plane of the microlens array.
Figure 18B:
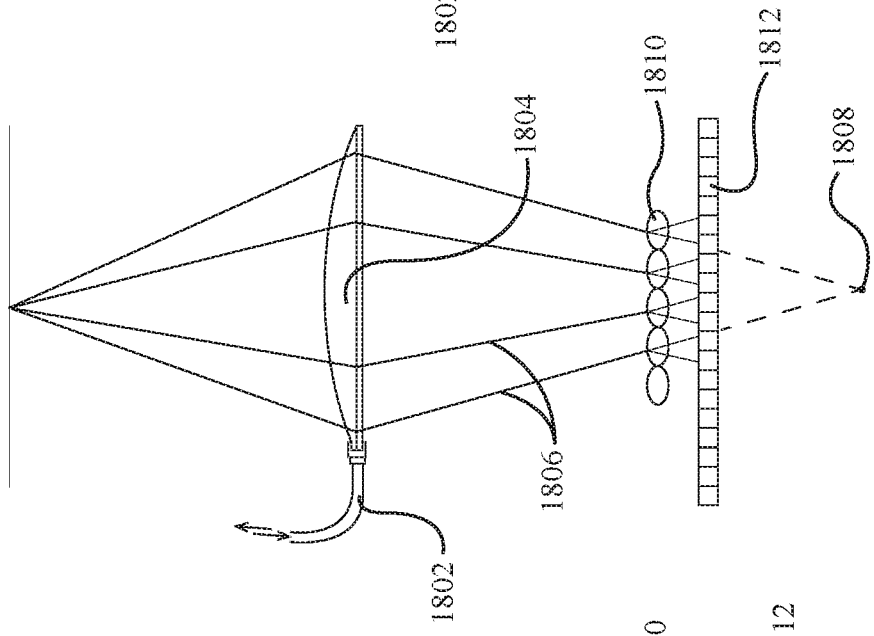
FIG. 18b is another diagrammatic representation of the fluidic digital light field photography (DIFLFP) camera described herein, wherein the image of the object is being focused behind the plane of the microlens array.
Figure 18A:
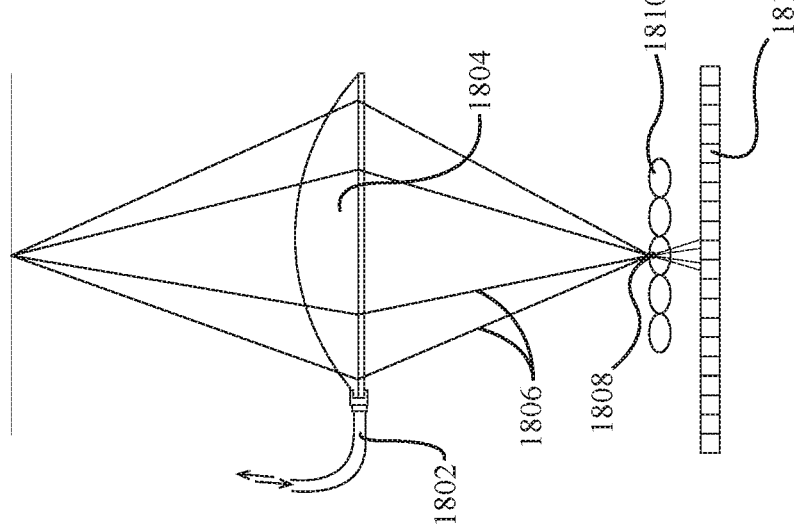
FIG. 18a is a diagrammatic representation of a fluidic digital light field photography (DIFLFP) camera described herein, wherein the image of an object is being focused on the plane of the microlens array, according to still another embodiment of the invention.
Figure 19:
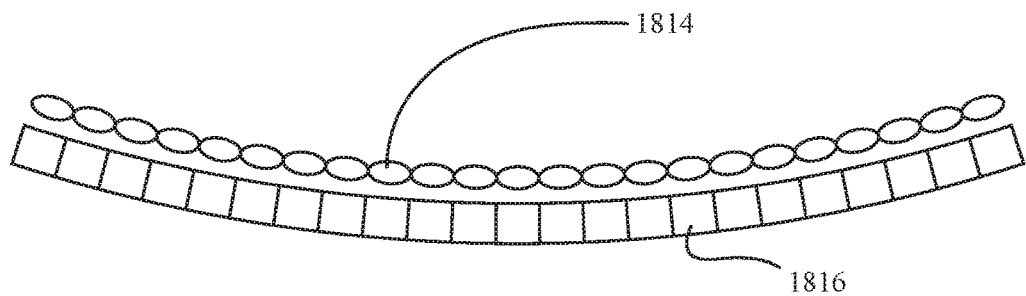
FIG. 19 is a diagrammatic representation of the concave microlens and sensor array of the fluidic digital light field photography (DIFLFP) camera described herein.

In one or more illustrative embodiments of the light field camera using a fluidic lens, the digital in-focus, light field photography (DIFLFP) camera provides a variable field of view and variable focal points from the objective tunable lens, in one second to a millisecond, from an object located just in front of the objective lens to infinity, as the light rays pass through a microlens array in the back of the camera and a layer of sensors made of light sensitive quantum dots, which along with microlens layer, create a concave structure (refer to FIG. 19). As such, the lens generates more light and signal information from variable focal points of the flexible fluidic lens that are capable of being used by a software algorithm of a processor so as to produce 2-3-4 D images in real-time or video. The generated images reduce the need for loss of light, which occur in refocusing the rays in standard light field cameras, but use the direction and intensity of light rays to obtain a sharp image from any distance from the lens surface to infinity, thereby producing in one cycle of changing the focal point of a tunable or hybrid fluidic objective lens of the camera electronically, or using simultaneously a microfluidic pump creating a maximum convexity in the lens to least amount and return. FIGS. 18*a*-18*c* illustrate the varying focal point 1808 that may be achieved by the fluidic digital light field photography (DIFLFP) camera. In FIG. 18*a*, the image of the object located outside is focused on the plane of the microlens array and the light rays 1806 are stimulating different sensors 1812 located in the back of the microlens array 1810. Changes in the configuration of the light rays 1806 are produced by decreasing or increasing the amount of the fluid injected into the chamber of the fluidic objective lens 1804 via the fluid pipe 1802, thereby producing a change in the focal point 1808 and the configuration of the light rays 1806 in the camera and their recording pattern focal in the DIFLFP camera. In FIG. 18*b*, the image of the object located outside is focused behind the plane of the microlens array 1810, while in FIG. 18*c*, the image of the object located outside is focused in front of the plane of the microlens array 1810. FIG. 19 illustrates the curved plane of the microlens array 1814 and sensor array 1816 that slopes upward to capture the side rays coming from the periphery of the fluidic objective lens, according to one embodiment of the fluidic light field camera.

Figure 20:
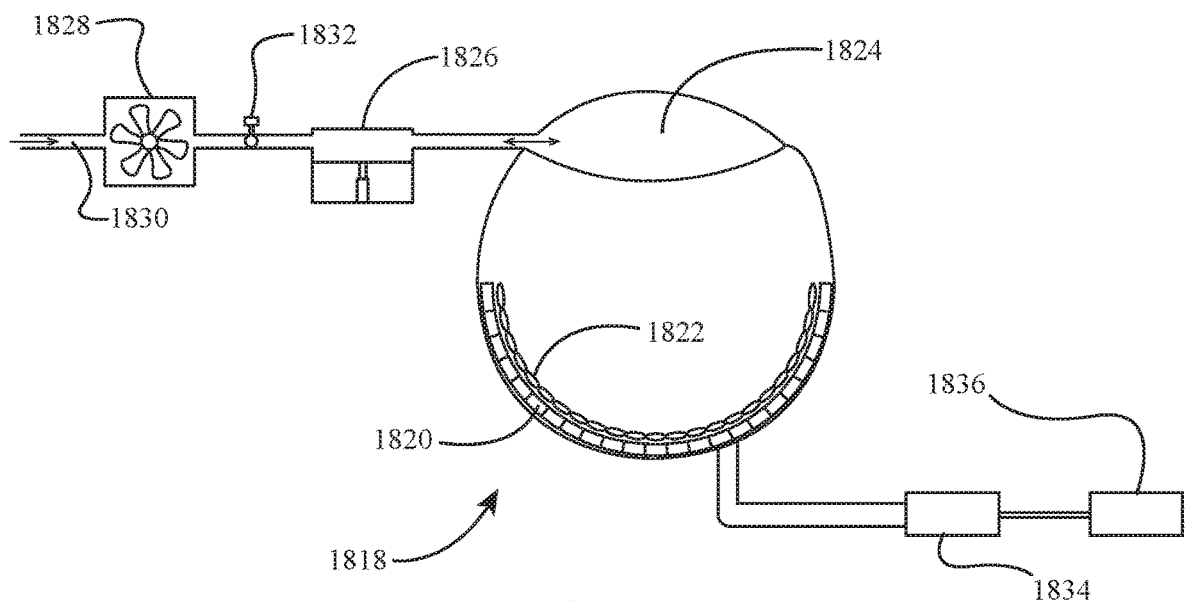
FIG. 20 is a diagrammatic representation of another fluidic light field camera described herein, according to yet another embodiment of the invention.

Another exemplary fluidic light field camera 1818 is illustrated in FIG. 20. As shown in this figure, fluidic light field camera 1818 includes a concave sensor array 1820, a concave microlens array 1822 disposed in front of the concave sensor array 1820, and a fluidic or tunable lens 1824 disposed in front of the concave sensor and microlens arrays 1820, 1822. In FIG. 20, it can be seen that the sensor array 1820 is operatively coupled to one or more processors 1834 and/or one or more computers 1836 for processing the image data acquired from the sensor array 1820. In the illustrative embodiment, the fluidic or tunable lens 1824 of the fluidic light field camera 1818 may be in the form of a hybrid fluidic lens that is capable of changing from plus to minus diopters, which may include a secondary electromagnetic system for fine tuning of lens 1824 that is provided in addition to the primary fluidic system used for the coarse adjustments of the lens 1824. A pump 1828, which is connected to inlet pipe 1830, is provided for aspiration and injection of a fluid into the fluidic lens 1824 in order to change the shape of the fluidic lens 1824. Also, as shown in FIG. 20, a fluid control device 1826, which contains an actuator driven by a servomotor or piezoelectric system, is provided between the pump 1828 and fluidic lens 1824. In addition, in FIG. 20, it can be seen that a valve 1832 is provided between the pump 1828 and the fluid control device 1826. When the valve 1832 is closed, a constant amount of the fluid is maintained in the fluid control system, thus allowing minor adjustments to be made to the shape of the lens 1824 using the fluid control device 1826 (i.e., the linear actuator in the fluid control device 1826 is driven up or down by the servomotor or piezoelectric system so as to change the fluid containment volume of the fluid control device 1826, and thus change the volume of fluid in the fluidic lens 1824). Rather than using the fluid control device 1826 to minor adjustments to the shape of the lens 1824, minor adjustments may also be made to the shape of the lens 1824 using a secondary electromagnetic system (i.e., when the valve 1832 is closed). The valve 1832 is open when the pump 1828 is being used to increase or decrease the volume of fluid in the chamber of the fluidic lens 1824.

Figure 21:
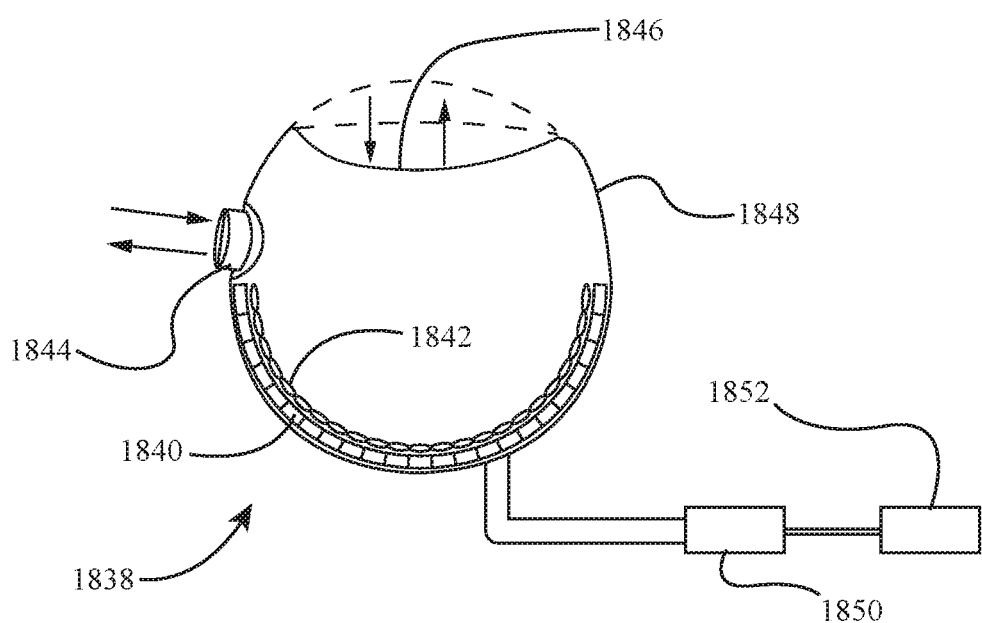
FIG. 21 is a diagrammatic representation of yet another fluidic light field camera described herein, according to still another embodiment of the invention.

Yet another exemplary fluidic light field camera 1838 is illustrated in FIG. 21. Similar to the fluidic light field camera 1818 described above with respect to FIG. 20, fluidic light field camera 1838 of FIG. 21 includes a concave sensor array 1840, a concave microlens array 1842 disposed in front of the concave sensor array 1840, and a fluidic or tunable lens 1846 disposed in front of the concave sensor and microlens arrays 1840, 1842. As described above for the camera of FIG. 20, it can be seen that the sensor array 1840 in FIG. 21 is operatively coupled to one or more processors 1850 and/or one or more computers 1852 for processing the image data acquired from the sensor array 1840. Unlike the camera 1818 described above, the fluidic objective lens 1846 comprises a single flexible membrane mounted in an opening defined by a rigid outer wall 1848 of the fluidic light field camera 1838. The fluid chamber of the camera 1838 is open to the space containing the sensor array 1840 and the microlens array 1842 in the camera 1838, and a fluid control device 1844 (e.g., in the form of a servomotor or piezoelectric system driving a piston) that is used to pressurize or depressurize the fluid chamber so as to displace the flexible membrane 1846 accordingly. In the illustrative embodiment of FIG. 21, a needle, for injection and withdrawing of the fluid from the chamber, may be placed inside the chamber behind the membrane 1846 to move the membrane 1846 forward and backward at any place.

In the embodiments described herein, the fluid described in conjunction with the fluidic lens broadly refers to any type of fluid, such as air or a liquid. Also, in the embodiments described herein, the light rays entering the fluidic light field camera may comprise any wavelength of light (e.g., from ultraviolet to infrared).

In one or more embodiments, the fluidic lens is dynamic because the plane of the image inside the camera moves forward or backward with each electric pulse applied to the piezoelectric or a microfluidic pump motor transmitting a wave of fluid flow inside or aspirating the fluid from the lens cavity so that the membrane returns to the original position, thereby creating either a more or less a convex lens, or a minus lens when the back side has a glass plate with a concave shape.

In one embodiment, the lens of the light field camera is only a flexible transparent membrane that covers the opening of the camera's cavity in which the fluid or air is injected or removed so as to create a convex or concave surface using a simple piezoelectric attachment that can push the wall of the camera locally inward or outward thereby forcing the transparent membrane that acts like a lens to be convex or concave and changes in the focal point from a few millimeters (mm) to infinity and return while all data points are recorded and analyzed by its software.

In one or more embodiments of the light field camera with the fluidic lens, the light rays entering the camera pass through the microlenses located in the back of the camera directly to the sensors made of nanoparticles, such as quantum dots (QDs) made of graphene, etc.

In one or more embodiments of the light field camera with the fluidic lens, the camera obtains a subset of signals from the right or left side of the microlens and sensor array separately to reconstruct the 3-D image from the information.

In one or more embodiments of the light field camera with the fluidic lens, the fluidic lens converts the light rays focused either anterior or posterior of the focal plane of the microlens/sensor plane to electrical signals, which are transmitted to the camera's processor with the software algorithm loaded thereon so that the images may be displayed as static 2-D or 3-D multispectral or hyperspectral images or so that a tomographic image or a video of a moveable object may be created.

In one or more embodiments of the light field camera with the fluidic lens, the right or left portion of the sensors are capable of displaying from either a slightly anterior or posteriorly located focal point to the microlens, thereby providing more depth to the image without losing the light intensity of the camera, as is the case with the standard light field camera having a static objective lens or a static membrane, which is entirely dependent on producing a virtual image obtained from a fixed focal point.

In one or more embodiments of the light field camera with the fluidic lens, a prismatic lens may be disposed between the microlens array and the sensors so that individual wavelengths may be separated to produce color photography or multispectral images including the infrared or near infrared images.

In one or more embodiments of the light field camera with the fluidic lens, the process of focusing and defocusing collects more light rays that may be used to create 2D or 3D or 4D images.

In one or more embodiments of the light field camera with the fluidic lens, the fluidic lens can change its surface by injecting and withdrawing the fluid from the lens and returning to its original shape in a time range of one second to less than a millisecond, thereby allowing the light rays to be recorded that pass through a single row or multiple rows of microlenses before reaching the sensor layer of quantum dots or monolayer of graphene or any semiconductor nanoparticles that absorb the light energy and convert it to an electrical signal.

In one or more embodiments of the light field camera, the flexible transparent membrane can change its surface by injecting and withdrawing the fluid/air from the cameras cavity and returning to its original shape in a time range of one second to less than a millisecond, thereby allowing the light rays to be recorded that pass through a single row or multiple rows of microlenses before reaching the sensor layer of quantum dots or monolayer of graphene or any semiconductor nanoparticles that absorb the light energy and convert it to an electrical signal.

In one or more embodiments of the light field camera with the fluidic lens, by pumping fluid in the fluidic microlens system, the field of the view of the lens is expanded and returns to its original position upon its relaxation. During this period of time, the light rays that have entered the system have passed through a series of microlenses which project the rays on a layer of photosensors (see e.g., FIGS. 18a-18c) to become stimulated, thereby creating an electrical current traveling to a processor or computer with a software algorithm loaded thereon to analyze and create a digital image from the outside world. In one or more embodiments, the microlens array of the fluidic lens may include a pluggable adaptor.

In one or more embodiments of the light field camera with the fluidic lens, the microlenses and the layer of sensors extend outward so as to create a concave structure inside the camera (see FIGS. 19-21), thereby permitting the incoming light rays of the peripheral field of view to be projected on the peripherally located microlens and sensors of the camera so as to be absorbed and transferred to the processor with the algorithm loaded thereon, which mathematically analyzes, manipulates, and records the light data so as to provide a combination of signals that shows the direction from which the rays emanated.

In one or more embodiments of the light field camera with the fluidic lens, the microlens array is in the form of graded-index (GRIN) lens array so as to provide excellent resolution.

In one or more embodiments of the light field camera with the fluidic lens or transparent flexible membrane, the microlens array is separated from another smaller nanosized lenses array attached to a filter, followed by the sensors to differentiate the color wavelength.

In one or more embodiments of the light field camera with the fluidic lens, the deformable objective lens, by changing its lens refractive power, its field of view, and its focus, transmits significantly more information, in one millisecond cycle, to the computer than a single static lens or simple lensless membrane with compressive sensing without microlenses is capable of doing, but also maintains more signals in its unlimited focal points sufficient data that is able to be easily reproduced or refocused instantaneously or later by the camera's software algorithms so as to create sharp images in 2-3 dimensions or 4 dimensions. However, the exposure time can be prolonged or shortened, as needed, by repeating the cycle of recording from less than one Hertz to >30 Hertz to thousands of Hertz or more enough for cinematography while the light rays pass through unlimited focal points of the lens back and forth of the sensors to the back of the lens covering a long distance from, a few mm to infinity achieving fast sharp images by retracing and mathematical reconstruction as compared to a photo taken from a camera with a solid fixed objective lens.

In one or more embodiments of the light field camera with the fluidic lens, the signals also can be analyzed by the algorithm of the computer located outside the camera for any object that is photographed at any given distance.

In one or more embodiments of the light field camera with the fluidic lens, the camera's processor or a computer can retrace the rays toward any direction of the light rays, thereby simultaneously eliminating refractive aberrations or motion blur while the light is focused over any distance before or beyond the focal point of the lens using the computer software.

In one or more embodiments, the fluidic light field camera will provide an immense amount of data during the short period of time that the lens membrane is displaced as a result of pumping fluid inside the system and withdrawing it, the forward and backward movement creating three dimensional images with depth of focus, which are easily recreated without sacrificing the resolution of the image or need for "focus bracketing" to extend the re-focusable range by capturing 3 or 5 consecutive images at different depths as is done in standard light field cameras with the complete parameterization of light in space as a virtual hologram.

In one or more embodiments, the objective lens of the digital light field photography (DIFLFP) camera is a fluidic lens in which the power of the lens varies from −3.00 to +30.00 dioptric power depending on the amount of fluid either injected or withdrawn with a micro-pump into the fluidic lens with an aperture of 2 to 10 millimeters (mm) or more.

In one or more embodiments, the objective lens is a liquid or tunable lens, such as an electrically and mechanically tunable lens controlling the focal length of the lens.

In one or more embodiments, the tunable lens is a liquid crystal, and molecules of the liquid crystal are capable of being rearranged using an electric voltage signal.

In one or more embodiments, the digital light field photography (DIFLFP) camera utilizes a hybrid lens, as described in Applicant's U.S. Pat. No. 9,671,607, which is incorporated by reference herein in its entirety. In such a hybrid lens, the increase or decrease of the fluid in the fluidic lens chamber occurs electronically with either a servo motor, or a piezoelectric system for a rapid response.

In one or more embodiments, the DIFLFP camera system obtains image and depth information at the same time.

In one or more embodiments, during the photography, the increase or decrease of the fluid in the fluidic lens is done in a high frequency changing the focal plane of the fluidic lens during the time which a million or billion light rays are sensed and recorded for analysis.

In one or more embodiments, the rays of the light are collected from a wide concave surface of the sensor arrays located behind hundreds of thousands of microlenses that curve up in the back of the camera during the change in the focal point of the fluidic lens, which also creates a wider field of view, producing millions to billions of electronic pulses from which the sharp wide field images or videos are reconstructed by the specially programmed computer in a 2-3-4 dimensional manner from the objects at any desired distance in the field of view without losing the sharpness of the image.

In one or more embodiments, the DIFLFP camera captures light from a wider field that increases or decreases the field of view rather than fixed objective lenses or compressive cameras with their assembly apertures.

In one or more embodiments, the objective lens is a composite lens of fluidic and a solid lens, a diffractive lens or a liquid crystal coating with electronic control of its refractive power.

In one or more embodiments, the microlenses are replaced with transparent photosensors where the sensors directly communicate with the processor and software algorithm to build desired images.

In one or more embodiments, the solid lens is located behind the flexible membrane of the fluidic lens or inside the fluidic lens providing a wider field of view and higher magnification.

In one or more embodiments, the additional lens can be a convex or a concave lens to build a Galilean or astronomical telescope.

In one or more embodiments, the lens is replaced with a flexible membrane that is capable of moving forward or backward and having on its surface a two dimensional aperture assembly providing a wider field of view when the lens becomes more convex pushing the membrane's surface forward than the standard lensless light field cameras.

In still one or more further embodiments, the objective lens of the light field camera is only a transparent flexible membrane supported by the outer housing of the camera's cavity, or housing defining the camera's chamber which receives a fluid therein (e.g., air or another gas) through a cannula. When the fluid is injected in the camera's cavity, the flexible transparent membrane bulges out acting as convex lens, and when the fluid is withdrawn from the camera's cavity, the membrane becomes a flat transparent surface, then assumes a concave shape and acts as a minus lens when the light passes through it to reach the lenslets and the sensors in the back of the fluidic field camera that are connected to a processor.

In one or more embodiments of the DIFLFP camera, there are numerous microlenses in the focal plane of the liquid lens.

In one or more embodiments, the microlenses are 3-D printed to less than 1 micrometer in diameter, lens structure, and are nanolenses of less than 10 nanometers (nm).

In one or more embodiments, the microlenses are 3-D printed from silicone, or any other transparent polymer.

In one or more embodiments, the sensors are 3-D printed and placed in the camera.

In one or more embodiments, the camera wall is 3-D printed.

In one or more embodiments, the two dimensional microlens plane ends slightly forward forming a concave plane to capture more light from the peripheral objective lens surfaces areas of the liquid lens as it moves forward and backward.

In one or more embodiments, the plane of the sensor array follows the curvature of the forwardly disposed microlens plane for building a concave structure (refer to FIGS. 19-21).

In one or more embodiments of the DIFLFP camera, the light sensors obtain information on the direction and light intensity from a wide field of view.

In one or more embodiments, the sensors provide electronic pulse information to a processor or a computer, equipped with a software algorithm to produce desired sharp monochromatic or color 2-4 D images.

In one or more embodiments, the computer is powerful enough to obtain a million or billion bits of information, having a software algorithm to provide images from any object located in the field of view before or behind a photographed object ranging from a very short distance from the objective lens surface to infinity.

In one or more embodiments of the DIFLFP camera, the computer and its software algorithm is capable of producing 2-3-4 dimensional sharp images, with desired magnification, and in color form, for any object located in front of the camera.

In one or more embodiments, the camera can provide an instant video in a 2-3 D image projected on an LCD monitor located in the back of the camera.

In one or more embodiments, the photos or videos captured using the camera are sent electronically via the internet to another computer using the GPU system, etc.

In one or more embodiments, using DIFLFP live video, time-related images can be presented in the fourth dimension with real-time high speed processing. To achieve high speed processing, a graphics processing unit (GPU), a programmable logic chip or field programmable gate array (FPGAs) may be provided along with a high-performance processor as VLIW (Very Long Instruction Word) core and a digital signal processor (DSP) microprocessor.

In one or more embodiments, the DIFLFP camera is used for visualization of a live surgery that can be projected in 3-4 D using the fluidic lens light field camera in the operating microscope that is simultaneously projected back onto the ocular lenses of the operating microscope or used in robotic surgery of brain, heart, prostate, knee or any other organ with robotic surgery, electronic endoscope system, 3D marking in laser processing systems, barcode scanning, automated inspection with a distance sensor, in neuroscience research, documenting the nerves or in retinal photography where the eye cannot be exposed to the light for a long time or when long exposure time is needed in low light photography, or variable spot size in light emitting diode (LED) lighting.

In one or more embodiments, the DIFLFP camera has a distance sensor controlling the initial start of the image focused on a certain object in the field of DIFLFP field and can be used in macro or microphotography and having a liquid crystal display (LCD) touch screen.

In one or more embodiments, the wavefront phase and the distance from the object is calculated by the software measuring the degree of focusing required for two rays to focus.

In one or more embodiments, the DIFLFP camera is used for the creation of augmented reality and virtual reality.

In one or more embodiments, the DIFLFP camera is used with additional lenses in tomographic wavefront sensors, measuring amplitude and phase of the electromagnetic field.

In one or more embodiments, the DIFLFP camera can generate stereo-images for both eyes of the user to see objects stereoscopically.

In one or more embodiments, the DIFLFP camera is equipped with an auto sensor to focus on a moving object, such as in sport activities or in dynamic facial recognition.

Any of the features or attributes of the above described embodiments and variations can be used in combination with any of the other features and attributes of the above described embodiments and variations as desired.

Although the invention has been shown and described with respect to a certain embodiment or embodiments, it is apparent that this invention can be embodied in many different forms and that many other modifications and variations are possible without departing from the spirit and scope of this invention.

Moreover, while exemplary embodiments have been described herein, one of ordinary skill in the art will readily appreciate that the exemplary embodiments set forth above are merely illustrative in nature and should not be construed as to limit the claims in any manner. Rather, the scope of the invention is defined only by the appended claims and their equivalents, and not, by the preceding description.

The invention claimed is:

1. A fluidic light field camera, comprising:
a fluidic objective lens, the fluidic objective lens having an outer housing and a flexible membrane supported within the outer housing, the flexible membrane at least partially defining a chamber that receives a fluid therein;
a fluid control system operatively coupled to the fluidic objective lens, the fluid control system configured to insert an amount of the fluid into the chamber of the fluidic objective lens, or remove an amount of the fluid from the chamber of the fluidic objective lens, in order to change the shape of the fluidic objective lens in accordance with the amount of fluid therein;
a microlens array disposed behind the fluidic objective lens, the microlens array including a plurality of microlenses, the plurality of microlenses configured to capture light rays entering the fluidic light field camera from varying distances away from the fluidic light field camera;
a sensor array disposed behind the microlens array, the sensor array including a plurality of pixels, the plurality of microlenses configured to divert the light rays to different ones of the pixels of the sensor array so as to provide directional information for the light rays entering the fluidic light field camera; and
a data processing device operatively coupled to the fluid control system and the sensor array, the data processing device configured to vary the focal point of the fluidic light field camera by using the fluid control system to control the shape of the fluidic objective lens, thereby enabling all portions of an image being captured by the fluidic light field camera to be in focus during a single recording cycle of the fluidic light field camera, and the data processing device further configured to vary the focal point of the fluidic light field camera in a time duration of less than one millisecond so that the fluidic light field camera is capable of creating a two-dimensional image, a three-dimensional image, and/or a video where all portions of the image or images being captured by the fluidic light field camera are in focus during the single recording cycle of the fluidic light field camera.

2. The fluidic light field camera according to claim 1, wherein the fluid control system comprises a pump and one or more fluid distribution lines, at least one of the one or more fluid distribution lines fluidly coupling the pump to the fluidic objective lens so that the pump is capable of adjusting concavity and/or convexity of the fluidic objective lens.

3. The fluidic light field camera according to claim 1, wherein the fluid control system comprises a servomotor or piezoelectric system for driving an actuator that is configured to adjust concavity and/or convexity of the fluidic objective lens.

4. The fluidic light field camera according to claim 1, wherein the fluidic objective lens further comprises a magnetically actuated subsystem configured to selectively deform the flexible membrane so as to increase or decrease the convexity of the flexible membrane of the fluidic objective lens.

5. The fluidic light field camera according to claim 4, wherein the magnetically actuated subsystem of the fluidic light field camera comprises an annular or rectangular ring-shaped plate disposed on a front surface of the flexible membrane and a corresponding annular or rectangular ring-shaped electromagnet disposed on a rear surface of the outer housing or flexible membrane, the annular or rectangular ring-shaped electromagnet configured to selectively displace the annular or rectangular ring-shaped plate disposed on the front surface of the flexible membrane when an electrical current is selectively applied to the electromagnet, whereby the selective displacement of the annular or rectangular ring-shaped plate by the electromagnet increases or decreases the convexity of the flexible membrane.

6. The fluidic light field camera according to claim 1, wherein the microlens array and the sensor array are disposed in a concave configuration relative to the light rays entering the fluidic light field camera through the fluidic objective lens.

7. A fluidic light field camera, comprising:
a housing, the housing having a front portion and a rear portion;
a fluidic objective lens disposed in the front portion of the housing, the fluidic objective lens having a flexible membrane supported by the housing, the flexible membrane at least partially defining a chamber that receives a fluid therein;
a fluid control system operatively coupled to the fluidic objective lens, the fluid control system configured to insert an amount of the fluid into the chamber of the fluidic objective lens, or remove an amount of the fluid from the chamber of the fluidic objective lens, in order to change the shape of the fluidic objective lens in accordance with the amount of fluid therein;
a microlens array disposed in the rear portion of the housing behind the fluidic objective lens, the microlens array including a plurality of microlenses, the plurality of microlenses configured to capture light rays entering the fluidic light field camera from varying distances away from the fluidic light field camera;
a sensor array disposed in the rear portion of the housing behind the microlens array, the sensor array including a plurality of pixels, the plurality of microlenses configured to divert the light rays to different ones of the pixels of the sensor array so as to provide directional information for the light rays entering the fluidic light field camera; and
a data processing device operatively coupled to the fluid control system and the sensor array, the data processing device configured to vary the focal point of the fluidic light field camera by using the fluid control system to control the shape of the fluidic objective lens, thereby enabling all portions of an image being captured by the fluidic light field camera to be in focus during a single recording cycle of the fluidic light field camera;
wherein the microlens array and the sensor array are disposed in a concave configuration relative to the light rays entering the fluidic light field camera through the fluidic objective lens so as to capture more light from a peripheral portion of the fluidic objective lens.

8. The fluidic light field camera according to claim 7, wherein the fluid control system comprises a pump and one or more fluid distribution lines, at least one of the one or more fluid distribution lines fluidly coupling the pump to the fluidic objective lens so that the pump is capable of adjusting concavity and/or convexity of the fluidic objective lens.

9. The fluidic light field camera according to claim 7, wherein the fluid control system comprises a servomotor or piezoelectric system for driving an actuator that is configured to adjust concavity and/or convexity of the fluidic objective lens.

10. The fluidic light field camera according to claim 7, wherein the fluidic objective lens further comprises a magnetically actuated subsystem configured to selectively deform the flexible membrane so as to increase or decrease the convexity of the flexible membrane of the fluidic objective lens.

11. The fluidic light field camera according to claim 10, wherein the magnetically actuated subsystem of the fluidic light field camera comprises an annular or rectangular ring-shaped plate disposed on a front surface of the flexible membrane and a corresponding annular or rectangular ring-shaped electromagnet disposed on a rear surface of the outer housing or flexible membrane, the annular or rectangular ring-shaped electromagnet configured to selectively displace the annular or rectangular ring-shaped plate disposed on the front surface of the flexible membrane when an electrical current is selectively applied to the electromagnet, whereby the selective displacement of the annular or rectangular ring-shaped plate by the electromagnet increases or decreases the convexity of the flexible membrane.

12. The fluidic light field camera according to claim 7, wherein the data processing device is configured to vary the focal point of the fluidic light field camera in a time duration of less than one millisecond so that the fluidic light field camera is capable of creating a two-dimensional image, a three-dimensional image, and/or a video where all portions of the image or images being captured by the fluidic light field camera are in focus during the single recording cycle of the fluidic light field camera.

13. A tunable light field camera, comprising:
a housing, the housing having a front portion and a rear portion;
a tunable objective lens disposed in the front portion of the housing;
a control system operatively coupled to the tunable objective lens, the control system configured to change the shape of the tunable objective lens;
a microlens array disposed in the rear portion of the housing behind the tunable objective lens, the microlens array including a plurality of microlenses, the plurality of microlenses configured to capture light rays entering the tunable light field camera from varying distances away from the tunable light field camera;
a sensor array disposed in the rear portion of the housing behind the microlens array, the sensor array including a plurality of pixels, the plurality of microlenses configured to divert the light rays to different ones of the pixels of the sensor array so as to provide directional information for the light rays entering the tunable light field camera; and
a data processing device operatively coupled to the control system and the sensor array, the data processing device configured to vary the focal point of the tunable light field camera by using the control system to control the shape of the tunable objective lens, thereby enabling all portions of an image being captured by the tunable light field camera to be in focus during a single recording cycle of the tunable light field camera;
wherein the microlens array and the sensor array are disposed in a concave configuration relative to the light rays entering the tunable light field camera through the tunable objective lens so as to capture more light from a peripheral portion of the tunable objective lens.

\* \* \* \* \*